(12) United States Patent
Verkman et al.

(10) Patent No.: US 11,123,340 B2
(45) Date of Patent: Sep. 21, 2021

(54) SMALL-MOLECULE UT-A-SELECTIVE UREA TRANSPORT INHIBITORS

(71) Applicant: The Regents of the University of California, Oakland, CA (US)

(72) Inventors: Alan S. Verkman, San Francisco, CA (US); Cristina Esteva-Font, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/560,880

(22) Filed: Sep. 4, 2019

(65) Prior Publication Data

US 2020/0016147 A1  Jan. 16, 2020

Related U.S. Application Data

(62) Division of application No. 15/310,061, filed as application No. PCT/US2015/029959 on May 8, 2015, now abandoned.

(60) Provisional application No. 61/991,112, filed on May 9, 2014.

(51) Int. Cl.
| | |
|---|---|
| *A61K 31/4709* | (2006.01) |
| *A61K 31/425* | (2006.01) |
| *A61K 31/426* | (2006.01) |
| *A61K 31/427* | (2006.01) |
| *A61K 31/47* | (2006.01) |

(52) U.S. Cl.
CPC ........ *A61K 31/4709* (2013.01); *A61K 31/425* (2013.01); *A61K 31/426* (2013.01); *A61K 31/427* (2013.01); *A61K 31/47* (2013.01)

(58) Field of Classification Search
CPC .............. A61K 31/4709; A61K 31/425; A61K 31/426; A61K 31/427; A61K 31/47
See application file for complete search history.

(56) References Cited

U.S. PATENT DOCUMENTS

| | | |
|---|---|---|
| 5,780,473 A | 7/1998 | Murugesan et al. |
| 2004/0054009 A1 | 3/2004 | Knobelsdorf et al. |
| 2010/0305105 A1 | 12/2010 | Verkman et al. |

OTHER PUBLICATIONS

Esteva-Font et al., "Diuresis and reduced urinary osmolality in rats produced by small-molecule UT-A-selective urea transport inhibitors," *The FASEB Journal* 28(9):3878-3890, 2017. (14 pages).
International Search Report and Written Opinion, dated Sep. 15, 2015, for International Application No. PCT/US2015/029959. (9 pages).
Ito et al., "A medium-term rat liver bioassay for rapid in vivo detection of carcinogenic potential of chemicals," *Cancer Science* 94(1):3-8, 2003.
PubChem, Compound Summary for CID 43955512, Jul. 21, 2009, URL=https://pubchem.ncbi.nlm.nih.gov/compound/4395512, download date Aug. 21, 2015. (9 pages).
PubChem, Compound Summary for CID 7635584, F2761-0007, Jul. 29, 2006, URL=https://pubchem.ncbi.nlm.nih.gov/compound/7635584, download date Aug. 21, 2015 (10 pages).
Rashad et al., "Facile Synthesis and Preliminary Structure-Activity Analysis of New Sulfonamides Against *Trypanosoma brucei*," *ACS Medicinal Chemistry Letters* 5:496-500, 2014.
STN Registry No. 946260-91-9, "Benzenesulfonamide, N-[4-chloro-3-(1,1-dioxido-2-isothiazolidinyl)phenyl]-2-methoxy-5-methyl-(CA Index Name)," Sep. 7, 2007. (1 page).

*Primary Examiner* — Alicia L Otton
(74) *Attorney, Agent, or Firm* — Seed IP Law Group LLP

(57) ABSTRACT

Provided herein are compounds that are urea transporter-A inhibitors that are useful for producing a strong diuretic response and may be used for treating refractory edema associated with cardiovascular, renal, and metabolic diseases, disorders, and conditions.

7 Claims, 18 Drawing Sheets

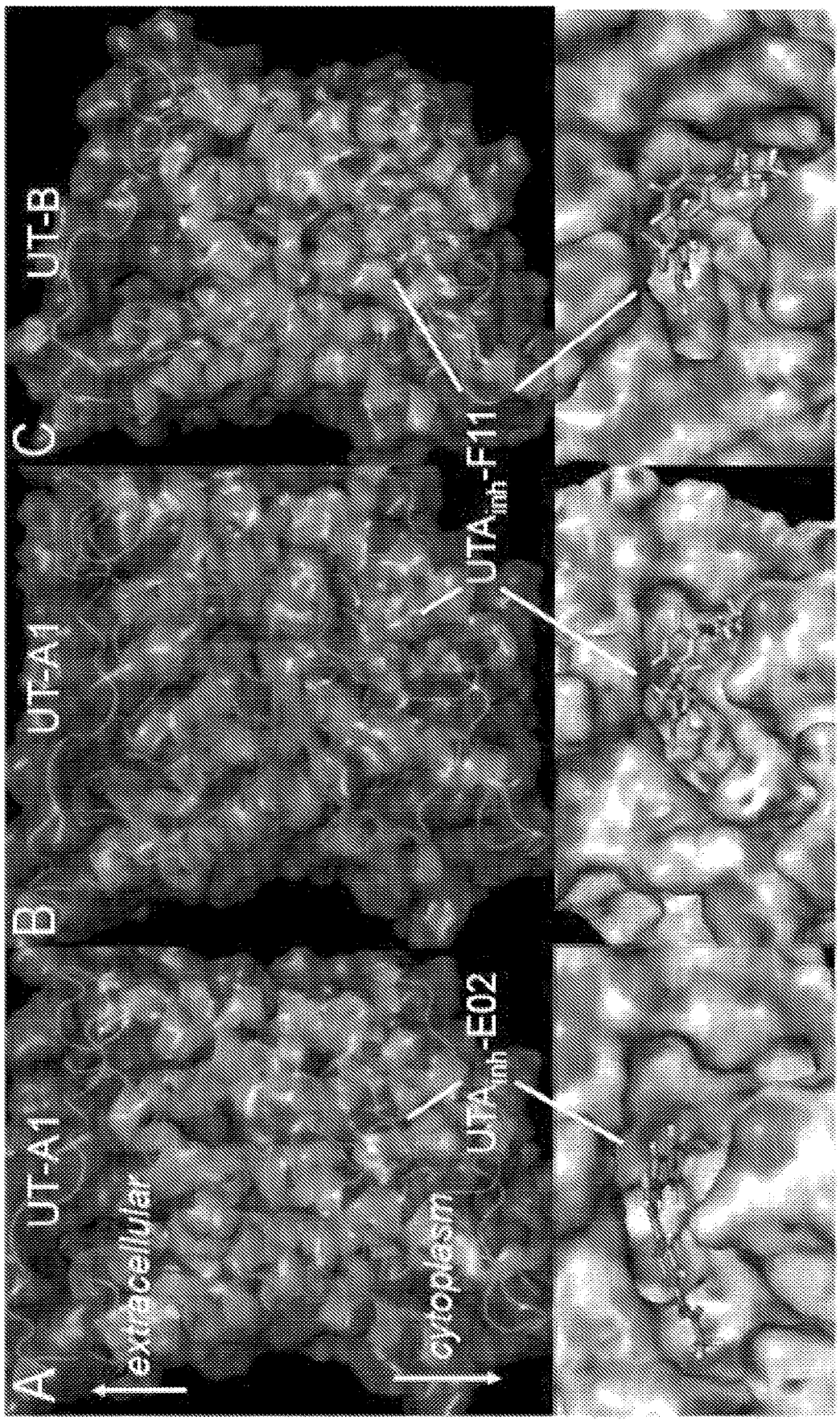

SMALL-MOLECULE UT-A-SELECTIVE UREA TRANSPORT INHIBITORS

CROSS-REFERENCES TO RELATED APPLICATIONS

This application is a divisional application of U.S. patent application Ser. No. 15/310,061, filed Nov. 9, 2016; which is a national stage application of PCT/US2015/029959, filed May 8, 2015; which claims the benefit under 35 U.S.C. § 119(e) of U.S. Provisional Patent Application No. 61/991,112, filed May 9, 2014, which applications are incorporated herein by reference in their entireties.

STATEMENT OF GOVERNMENT INTEREST

This invention was made with government support under Grant Nos. DK101373 and DK035124, awarded by the National Institutes of Health. The government has certain rights in this invention.

BACKGROUND

Technical Field

Compounds that inhibit urea transporters and methods for using these agents are described herein.

Description of the Related Art

Urea is generated by the liver as the major end product of nitrogen metabolism, released into the blood, and excreted by the kidneys. The processing of urea by the kidney is complex, involving countercurrent multiplication and exchange mechanisms that greatly increase urea concentration in the renal medulla compared to serum. In the maximally concentrating (antidiuretic) kidney, urea concentration in the urine can reach >1000 mM in mammals (see, e.g., Bankir et al., "Urea and the kidney" In: *The Kidney.* 6th ed., edited by Brenner B M, Philadelphia, (WB Saunders, 2000), 637-679; Sands et al., *Semin Nephrol* 29:178-95, 2009) much greater than the serum urea concentration of 4-10 mM.

The renal countercurrent mechanisms involve intrarenal urea recycling facilitated by urea transporters (UTs) expressed in renal tubule epithelial cells (UT-A, encoded by the SLc14A2 gene) and renal vasa recta microvessels (UT-B, encoded by the SLc14A1 gene) (see, e.g., Bagnasco, *Am J Physiol Renal Physiol* 284: F3-F10, 2003; Sands, *Curr Opin Nephrol Hypertens* 13:525-32, 2004; Shayakul et al., *Pflugers Arch* 447: 603-609, 2004; Stewart, *Br J Pharmacol* 2011 Mar. 30, doi:10.1111/j.1476-5381.2011.01377.x Epub ahead of print; Tsukaguchi et al., *J Clin Invest* 99:1506-15, 1997. Phenotype analysis of knockout mice lacking UT-B (see, e.g., Bankir et al., *Am J Physiol Renal Physiol* 286: F144-F151, 2004; Yang et al., *J Biol Chem* 277:10633-37, 2002) or various UT-A isoforms (see, e.g., Fenton et al., *Proc Natl Acad Sci U.S.A.* 101:7469-74, 2004; Fenton et al., *J Am Soc Nephrol* 16:1583-92, 2005; Uchida et al., *Mol Cell Biol* 25: 7357-63, 2005) has provided evidence for the involvement of UTs in the urinary concentrating mechanism, subject to the caveat that gene knockout may produce off-target effects such as compensatory changes in the expression of non-UT transport proteins (see, e.g., Fenton, *Curr Opin Nephrol Hypertens* 17:513-18, 2008; Klein et al., *J Am Soc Nephrol* 15:1161-67, 2004). Though UT function has been studied mainly in kidney, UTs are also expressed in erythrocytes, testis, brain, heart and urinary bladder (see, e.g., Doran et al., *Am J Physiol Regul Integr Comp Physiol* 290:R1446-R1459, 2006) where their physiological functions are not clear.

Diuretics are administered widely in humans to increase renal salt and water clearance in a variety of conditions that are associated with total body fluid overload, such as congestive heart failure and cirrhosis, as well in normovolemic states such as hypertension and syndrome of inappropriate secretion of antidiuretic hormone (SIADH). Most diuretics are inhibitors of salt absorption by kidney tubules, such as a furosemide block of $Na^+/K^+/2Cl^-$ co-transport in the thick ascending limb of Henle and a thiazide block of $Na^+/Cl^-$ co-transport in the distal tubule. Recently, a new type of diuretic, called an "aquaretic," has been developed to increase renal water clearance in hyponatremia associated with fluid overload or SIADH (see, e.g., Goldsmith, *Am. J. Cardiol.* 95:14B-23B (2005); Miller, *J. Am. Geriatr. Soc.* 54:345-53 (2006)). Vasopressin-2 receptor (V2R) antagonist aquaretics have been approved for clinical use in some countries, though not yet in the United States, and aquaporin inhibitor aquaretics are under development.

Functional studies in knock-out mice indicate a critical role for urea transporters (UTs) in the urinary concentrating mechanism and in renal urea clearance. However, potent and specific urea transport blockers have not been available. Accordingly, a third type of diuretic is needed: one that targets renal urea clearance mechanisms. Because urea is of at least equal importance to NaCl in the renal countercurrent mechanism for urinary concentration (see, e.g., Bankir et al., supra; Masilamani et al., *In The Kidney* (6th Edition), Brenner, ed. Philadelphia, Pa.; WB Saunders Company; pages 595-35; (2000)), such diuretics are needed for increasing solute clearance in states of fluid overload, hypertension, and may also be useful in prolonging dialysis-free survival in chronic renal insufficiency.

Urea transporter inhibitors identified to date have included non-selective membrane intercalating agents, urea analogs with insufficient potency, and specific urea transporter inhibitors with lower than desired potency. A need exists in the medical art for compounds that inhibit urea transporter and that exhibit nanomolar potency for increasing solute clearance and free water excretion in states of fluid overload, hypertension, and chronic renal insufficiency.

BRIEF SUMMARY

Compounds and methods are provided herein for treating diseases and disorders treatable by inhibiting a urea transporter. Provided herein are the following embodiments.

Embodiment 1

A pharmaceutical composition comprising a pharmaceutically acceptable excipient and a compound of Formula (II):

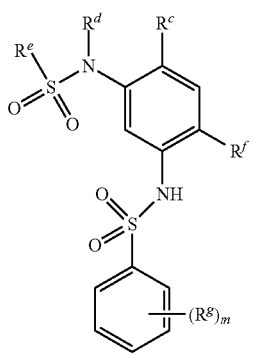

Formula (II)

wherein, m is 0, 1, 2 or 3;

$R^c$ is hydrogen, halo, or alkyl; or $R^c$ and $R^d$, together with the C and N atoms to which they are attached respectively, form a 5-member or 6-member heterocyclyl ring;

$R^e$ is alkyl; or $R^e$ and $R^d$, together with the S and N atoms to which they are attached respectively, form a 5-member or 6-member heterocyclyl ring;

$R^f$ is hydrogen or alkoxy; and $R^g$ is independently, at each occurrence, alkyl, alkoxy, or halo, a stereoisomer, enantiomer or tautomer thereof, a pharmaceutically acceptable salt thereof, or a prodrug thereof.

Embodiment 2

The pharmaceutical composition of Embodiment 1, comprising a pharmaceutically acceptable excipient and a compound of Formula (II):

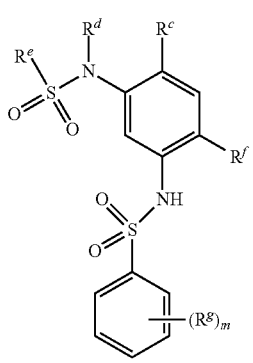

Formula (II)

wherein, m is 0, 1, 2 or 3;

$R^c$ is hydrogen, halo, or $C_{1-3}$alkyl; or $R^c$ and $R^d$, together with the C and N atoms to which they are attached respectively, form a 5-member or 6-member heterocyclyl ring;

$R^e$ is $C_{1-3}$alkyl; or $R^e$ and $R^d$, together with the S and N atoms to which they are attached respectively, form a 5-member or 6-member heterocyclyl ring;

$R^f$ is hydrogen or $C_{1-3}$ alkoxy; and $R^g$ is independently, at each occurrence, $C_{1-3}$alkyl, $C_{1-3}$alkoxy, or halo, a stereoisomer, enantiomer or tautomer thereof, a pharmaceutically acceptable salt thereof, or a prodrug thereof.

Embodiment 3

The pharmaceutical composition of Embodiment 1 or Embodiment 2, comprising a pharmaceutically acceptable excipient and a compound of Formula (IIa):

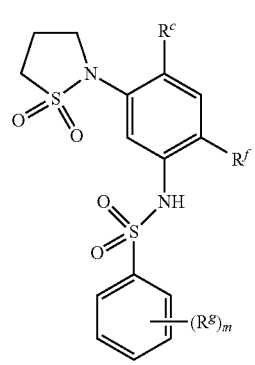

Formula (IIa)

wherein, m is 0, 1, 2 or 3;

$R^c$ is hydrogen, halo or $C_{1-3}$alkyl;

$R^f$ is hydrogen or $C_{1-3}$ alkoxy; and $R^g$ is independently, at each occurrence, $C_{1-3}$alkyl, $C_{1-3}$alkoxy, or halo, a stereoisomer, enantiomer or tautomer thereof, a pharmaceutically acceptable salt thereof, or a prodrug thereof.

Embodiment 4

The pharmaceutical composition of Embodiment 3 wherein, m is 2 or 3;

$R^c$ is hydrogen or chloro;

$R^f$ is methoxy; and $R^g$ is independently, at each occurrence, methyl, methoxy, fluoro or chloro.

Embodiment 5

The pharmaceutical composition of Embodiment 1 or Embodiment 2, comprising a pharmaceutically acceptable excipient and a compound of Formula (IIb):

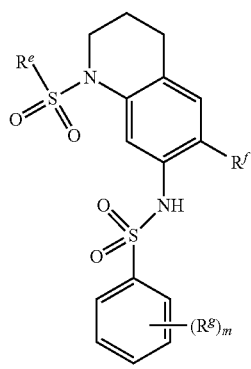

Formula (IIb)

wherein,
m is 0, 1, 2 or 3;
$R^e$ is $C_{1-3}$alkyl;
$R^f$ is hydrogen or $C_{1-3}$ alkoxy; and
$R^g$ is independently, at each occurrence, $C_{1-3}$alkyl, $C_{1-3}$alkoxy, or halo,
a stereoisomer, enantiomer or tautomer thereof, a pharmaceutically acceptable salt thereof, or a prodrug thereof.

Embodiment 6

The pharmaceutical composition of Embodiment 5 wherein
m is 0;
$R^e$ is $C_{1-3}$alkyl; and
$R^f$ is hydrogen.

Embodiment 7

A method for treating a disease or disorder treatable by inhibiting transport of urea in a subject, said method comprising administering to the subject the pharmaceutical composition according to any one of Embodiments 1-6.

Embodiment 8

The method of Embodiment 7 wherein the disease or disorder is selected from (a) refractory edema associated with cirrhosis, nephritic syndrome, acute renal failure, chronic renal insufficiency, or congestive heart failure; (b) syndrome of inappropriate antidiuretic hormone secretion (SIADH); (c) azotemia; (e) fluid retention; (f) hypertension, and (g) abnormal uresis.

Embodiment 9

A method for treating a disease or disorder treatable by inhibiting transport of urea in a subject, said method comprising administering to the subject pharmaceutical composition comprising a pharmaceutically acceptable excipient and a compound of Formula (I):

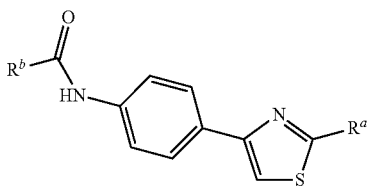

Formula (I)

wherein, $R^a$ is aryl, heteroaryl, cycloalkyl, or heterocyclyl; and
$R^b$ is alkyl,
a stereoisomer, enantiomer or tautomer thereof, a pharmaceutically acceptable salt thereof, or a prodrug thereof.

Embodiment 10

The method of Embodiment 9, said method comprising administering to the subject pharmaceutical composition comprising a pharmaceutically acceptable excipient and a compound of Formula (I):

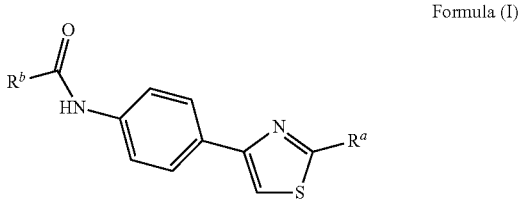

Formula (I)

wherein, $R^a$ is aryl, heteroaryl, cycloalkyl, or heterocyclyl; and
$R^b$ is methyl or ethyl,
a stereoisomer, enantiomer or tautomer thereof, a pharmaceutically acceptable salt thereof, or a prodrug thereof.

Embodiment 11

The method of Embodiment 9 or Embodiment 10 wherein $R^a$ is phenyl or indolyl.

Embodiment 12

The method of any one of Embodiments 9-11, wherein $R^b$ is methyl.

Embodiment 13

The method of any one of Embodiments 9-12 wherein the disease or disorder is selected from (a) refractory edema associated with cirrhosis, nephritic syndrome, acute renal failure, chronic renal insufficiency, or congestive heart failure; (b) syndrome of inappropriate antidiuretic hormone secretion (SIADH); (c) azotemia; (e) fluid retention; (f) hypertension, and (g) abnormal uresis.

Embodiment 14

Use of the pharmaceutical composition according to any one of Embodiments 1-6 for treating a disease or disorder treatable by inhibiting transport of urea.

Embodiment 15

Use of a pharmaceutical composition comprising a pharmaceutically acceptable excipient and a compound of Formula (I):

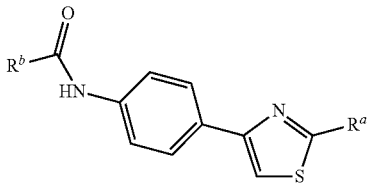

Formula (I)

wherein, $R^a$ is aryl, heteroaryl, cycloalkyl, or heterocyclyl; and
$R^b$ is alkyl,
a stereoisomer, enantiomer or tautomer thereof, a pharmaceutically acceptable salt thereof, or a prodrug thereof
for treating a disease or disorder treatable by inhibiting transport of urea.

Embodiment 16

Use of Embodiment 15 wherein the pharmaceutical composition comprises a pharmaceutically acceptable excipient and a compound of Formula (I):

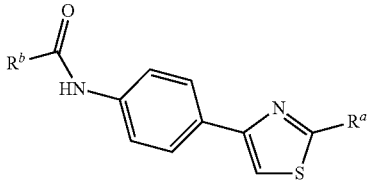

Formula (I)

wherein, $R^a$ is aryl, heteroaryl, cycloalkyl, or heterocyclyl; and
$R^b$ is methyl or ethyl,
a stereoisomer, enantiomer or tautomer thereof, a pharmaceutically acceptable salt thereof, or a prodrug thereof.

Embodiment 17

Use of Embodiment 15 or Embodiment 16 wherein $R^a$ is phenyl or indolyl.

Embodiment 18

Use of any one of Embodiments 15-17, wherein $R^b$ is methyl.

Embodiment 19

Use of any one of Embodiments 14-18, wherein the disease or disorder is selected from (a) refractory edema associated with cirrhosis, nephritic syndrome, acute renal failure, chronic renal insufficiency, or congestive heart failure; (b) syndrome of inappropriate antidiuretic hormone secretion (SIADH); (c) azotemia; (e) fluid retention; (f) hypertension, and (g) abnormal uresis.

In other embodiments, provided herein is a use of a compound of any one of structures (I), (II), (IIa) and (IIb) as described above and herein for the manufacture of a medicament for treating a disease or disorder treatable by inhibiting transport of urea, wherein the disease or disorder is selected from (a) refractory edema associated with cirrhosis, nephritic syndrome, acute renal failure, chronic renal insufficiency, or congestive heart failure; (b) syndrome of inappropriate antidiuretic hormone secretion (SIADH); (c) azotemia; (e) fluid retention; (f) hypertension, and (g) abnormal uresis.

In still another embodiment, provided herein is a compound of any one of structures (I), (II), (IIa) and (IIb) as described above and herein for use in treating a disease or disorder treatable by inhibiting transport of urea, wherein the disease or disorder is selected from (a) refractory edema associated with cirrhosis, nephritic syndrome, acute renal failure, chronic renal insufficiency, or congestive heart failure; (b) syndrome of inappropriate antidiuretic hormone secretion (SIADH); (c) azotemia; (e) fluid retention; (f) hypertension, and (g) abnormal uresis.

In still another embodiment, use of a compound of any one of structures (I), (II), (IIa) and (IIb) as described above and herein is provided herein for treating a disease or disorder treatable by inhibiting transport of urea, wherein the disease or disorder is selected from (a) refractory edema associated with cirrhosis, nephritic syndrome, acute renal failure, chronic renal insufficiency, or congestive heart failure; (b) syndrome of inappropriate antidiuretic hormone secretion (SIADH); (c) azotemia; (e) fluid retention; (f) hypertension, and (g) abnormal uresis.

Also provided herein in another embodiment, is a method for inhibiting transport of urea across a cell membrane comprising contacting a cell comprising a urea transporter-A and a compound having structures (I), (II), (IIa) and (IIb), as described above and herein.

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims that follow, the word "comprise" and variations thereof, such as, "comprises" and "comprising" are to be construed in an open, inclusive sense, that is, as "including, but not limited to." In addition, the term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features. Headings provided herein are for convenience only and do not interpret the scope or meaning of the claimed embodiments.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Also, as used in this specification and the appended claims, the singular forms "a," "an," and "the" include plural referents unless the content clearly dictates otherwise. Thus, for example, reference to "a compound" may refer to one or more compounds, or a plurality of such compounds, and reference to "a cell" or "the cell" includes reference to one or more cells and equivalents thereof (e.g., plurality of cells) known to those skilled in the art, and so forth. Similarly, reference to "a composition" includes a plurality of such compositions, and refers to one or more compositions unless the context clearly dictates otherwise.

When steps of a method are described or claimed, and the steps are described as occurring in a particular order, the description of a first step occurring (or being performed) "prior to" (i.e., before) a second step has the same meaning if rewritten to state that the second step occurs (or is performed) "subsequent" to the first step. The term "about" when referring to a number or a numerical range means that the number or numerical range referred to is an approximation within experimental variability (or within statistical experimental error), and thus the number or numerical range may vary between 1% and 15% of the stated number or numerical range. It should also be noted that the term "or" is generally employed in its sense including "and/or" unless the content clearly dictates otherwise.

BRIEF DESCRIPTION OF THE DRAWINGS

FIG. 1A: (top) Assay method showing rapid exposure of MDCK cells stably expressing UT-A1, AQP1 and YFP-H148Q/V163S to a 800-mM inward urea gradient. A decrease in cell volume (reduced fluorescence) due to AQP1-mediated water efflux is followed by cell swelling (increased fluorescence) due to urea and water influx. (bottom) Positive (phloretin curve) and negative (DMSO, 0 µM curve) controls shown with concentration-dependence data are shown for two active compounds. FIG. 1B: Summary of screening results. FIG. 1C: Chemical structures of UT-A inhibitors identified in the screen shown with prior reported UT-A inhibitors described in Esteva-Font et al. (2013) *Chem Biol.* 20, 1235-1244.

FIG. 2A: Concentration-inhibition data for UT-A1 inhibition by indicated compounds (mean±S.E., n=3). Fit to single-site inhibition model shown. FIG. 2B: Structural determinants of class E compounds for UT-A1 inhibition. (The substituents $R^1$ and $R^2$ are so named within FIG. 2B.) FIG. 2C: Structural determinants of class F compounds. FIG. 2D: Synthesis of UTA$_{inh}$-E02 and UTA$_{inh}$-F11. (a) EtOH, Et$_3$N, reflux, 45%; (b) 3-chloropropyl sulfonyl chloride, pyridine, CH$_2$Cl$_2$, 69%; (c) K$_2$CO$_3$, CH$_3$CN, 66%; (d) Pd/C, H$_2$, EtOH, 93%; (e) ArSO$_2$Cl (Ar may be, e.g., phenyl substituted with one or more substituents such as alkoxy or alkyl), pyridine, 60° C., 70%.

FIG. 3A: Reversibility studied by incubation with inhibitors (at 3 µM) with the transfected MDCK cells for 15 min, washing for 15 min, and then assay for UT-A1 inhibition. FIG. 3B: Urea competition studied by assay of UT-A1 inhibition using different urea concentrations (curves in left panels). Apparent IC$_{50}$ as a function of extracellular urea concentration, [urea]$_e$, at zero initial intracellular urea concentration (3$^{rd}$ panel), and as a function of intracellular urea concentration, [urea]$_i$, for fixed 1600 mM urea gradient (right panel). FIG. 3C: inhibition kinetics studied by assay of UT-A1 urea transport at different times after addition of 3 µM inhibitor (left). Summary of kinetic data (mean±S.E., n=3, right upper panel). Inhibitor permeability across MDCK cell monolayers on porous filters (mean±S.E., n=3, right lower panel). FIG. 3D: inhibitor selectivity studied by measurement of UT-B inhibition by an erythrocyte lysis assay in rat erythrocytes (top). UT-B concentration-inhibition data (bottom panels). FIG. 3E: Transepithelial urea transport in UT-A1-expressing MDCK cells. Cells were treated with 10 µM forskolin alone, forskolin+phloretin (0.7 mM), or forskolin plus inhibitor at 3 and 20 µM (mean±S.E., n=3).

FIGS. 4A-4C illustrates computational modeling of UT-A selective and non-selective inhibitors. Putative inhibitor binding sites on rat UT-A1 and rat UT-B based on functional measurements, homology modeling, and computational docking. Zoomed-in and zoomed-out representations of UTA$_{inh}$-E02 (FIG. 4A) and UTA$_{inh}$-F11 (FIG. 4B) bound to the rat UT-A1 cytoplasmic domain, and UTA$_{inh}$-F11 (FIG. 4C) bound to the rat UT-B cytoplasmic domain.

FIG. 5A: In vitro metabolic stability measured in rat hepatic microsomes. Kinetics of disappearance of indicated compounds (at 5 µM) following incubation with hepatic microsomes and NADPH, showing original LC/MS traces and time-course data (mean±S.E., n=3). FIG. 5B: Kinetics of plasma UTA$_{inh}$-E02 concentration following bolus intravenous administration of 5 mg UTA$_{inh}$-E02 in saline containing 20% dimethylacetamide and 40% γ-hydroxypropyl cyclodextrin (left panel). Original LC/MS traces shown in inset. UTA$_{inh}$-E02 concentration in urine collected at 0-3 and 3-6 h (second panel). Similar analysis done for UTA$_{inh}$-F11 following bolus intravenous administration of 5 mg in saline containing 20% dimethylacetamide and 0.6 mg/mL NaOH (two panels at the right). FIG. 5C: (left) Short-circuit current recordings. Cells were incubated at 37° C. for 10 min with 20 µM UTA$_{inh}$-E02 or 20 µM UTA$_{inh}$-F11 (or DMSO, vehicle) before addition of 20 µM forskolin and 100 µM ATP. (right) Summary of changes in short-circuit current ($\Delta I_{sc}$) produced by forskolin alone and forskolin+ATP (mean±S.E., n=3 cultures each).

FIG. 6A: Maximal urinary concentration was produced by dDAVP (4 µg/kg, IP, every 3 h) and dehydration. Inhibitors (5 mg) administered by intravenous injection at time 0. Urine volume (left) and osmolality (right) (mean±S.E., 4 rats per group) for indicated 3-h collections. FIG. 6B: Excretion of urea versus non-urea solutes (expressed as ratio) shown at baseline (−3 to 0 h collection) and after inhibitor treatment (0 to 6 h collection) (mean±S.E.). FIG. 6C: Study done as in A, but with control/hydrated rats (mean±S.E., 3 rats per group, *P<0.05, **P<0.01).

DETAILED DESCRIPTION

Figure 1A:
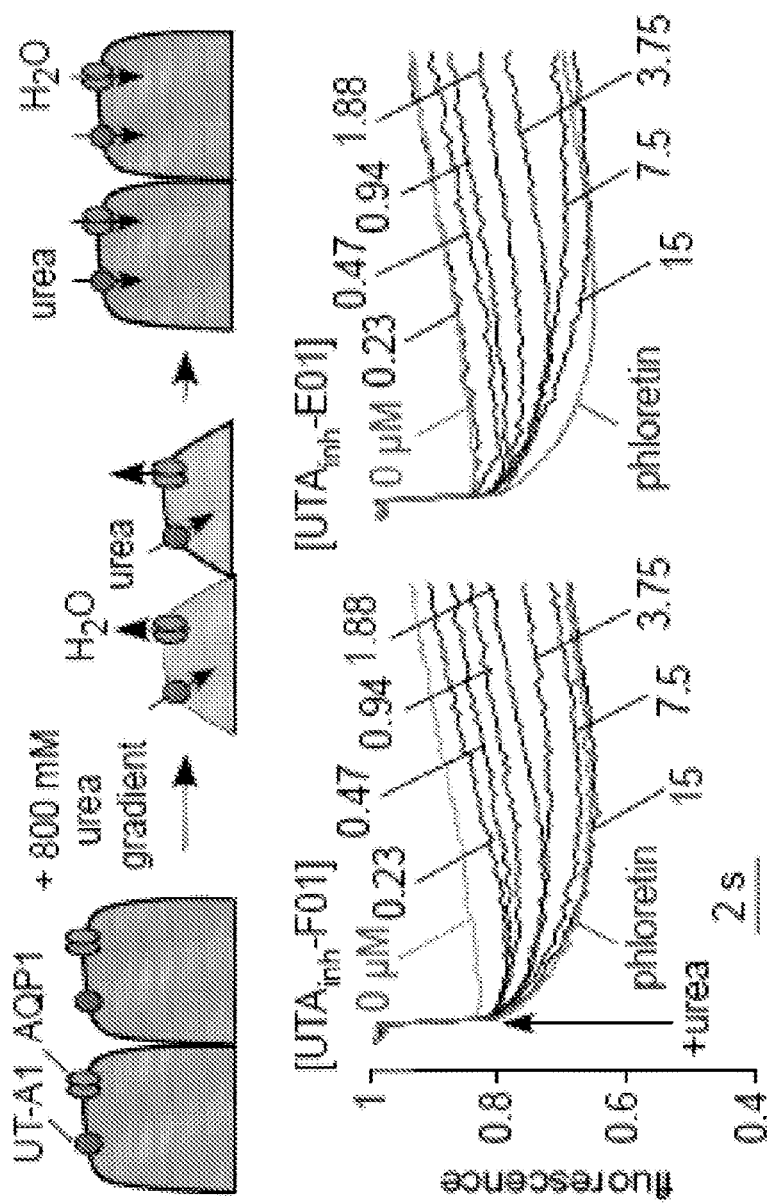
FIGS. 1A-1C presents results from high-throughput screening for identification of small molecules UT-A1 inhibitors.

As stated above, provided herein are compounds, compositions, and methods for treatment of one or more diseases or disorders treatable by inhibiting transport of a neutrally charged solute, such as urea, across a cell membrane by a urea transporter-A (UT-A). The compounds described herein are more potent UT-A inhibitors than compounds previously described and also exhibit improved metabolic stability.

Diseases, disorders, or conditions that may be treated according to the methods described herein may be associated with a fluid retention imbalance, such as urea clearance insufficiency. Potent, specific, small molecule inhibitors that selectively inhibit UT-A are described herein that may be used to treat diseases, disorders, or conditions treatable by administering a UT-A inhibitor. These UT-A inhibitors are salt-sparing diuretics, or 'urearetics', with a novel mechanism of action. UT-blocking diuretics may have utility alone, or in combination with conventional salt transport-blocking diuretics, in edema due to fluid overload (congestive heart failure, nephrotic syndrome and cirrhosis) and in hyponatremia due to chronic elevation in vasopressin (syndrome of inappropriate antidiuretic hormone secretion). Because of their unique mechanism of action on renal countercurrent multiplication, UT-A inhibitors (e.g., UT-A1 inhibitors) may be effective in states of refractory edema where conventional diuretics such as furosemide and thiazides have limited efficacy. Accordingly, the compounds described herein (i.e., compounds of structure (I), (II), (IIa) and (IIb)) may be useful for treating or preventing (i.e., reducing the likelihood of occurrence) of diseases or conditions including but not limited to a refractory edema associated with or caused by a cardiovascular, renal, or metabolic disease, disorder, or condition, such as cirrhosis, nephritic syndrome, acute renal failure, chronic renal insufficiency, and congestive heart failure. In certain other embodiments, the disease, disorder, or condition to be treated is syndrome of inappropriate antidiuretic hormone secretion (SIADH), azotemia, fluid retention, hypertension, and abnormal uresis. In other certain embodiments, at least one of the compounds of structure (I), (II), (IIa) and (IIb described herein may also be used in combination with a loop diuretic.

Defective urinary concentrating function in UT knockout mice suggests the potential utility of UT inhibitors as 'urearetics' that would impair urinary concentrating function by a mechanism different from that of salt-transport blocking diuretics such as furosemide, or aquaretics such as $V_2$-receptor antagonists. As found in mice, humans lacking UT-B manifest a modest urinary concentrating defect (see, e.g., Lucien et al., *J Biol. Chem.* 273:12973-80 (1998); Sands et al., *J Am. Soc. Nephrol.* 2:1689-96 (1992)). Previously available UT inhibitors included compounds that are nonspecific and exhibit moderate or low activity such as the non-specific membrane intercalating agent phloretin (exhibiting activity at >0.5 mM); urea analogs such as thiourea, methylurea, and dimethylurea (exhibiting activity at 50-100 mM); (see, e.g., Mayrand et al., supra), and chemically modified urea analogs (exhibiting irreversible activity at 30-100 µM) (Martial et al., Pflügers Arch. 423:51-58 (1993)).

The formation of concentrated urine by the kidney involves a countercurrent multiplication mechanism in which a hypertonic medullary interstitium is generated by the coordinated actions of salt, water and urea transporters (see, e.g., Bankir, L., and Yang, B. (2012) *Kidney Internat.* 81, 1179-1198; Sands, J M., and Layton, H E. (2009) *Semin Nephrol.* 29, 178-195; Sands, J M. (2007) *J Am Soc Nephrol.* 18, 670-671; Lei, T., Zhou, L., Layton, A T., Zhou, H., Zhao, X., Bankir, L., and Yang, B. (2011) *Am J Physiol Renal Physiol.* 301, F1251-F1259; Pannabecker, T L. (2013) *Am Physiol Regul Integr Comp Physiol.* 304, R488-R503). Urea transporter (UT) proteins of the UT-A class, encoded by the Slc14a2 gene, are expressed in tubule epithelial cells, and UT-B, encoded by the Slc14a1 gene, is expressed in vasa recta microvascular endothelial cells (see, e.g., Bagnasco, S M. (2003) *Am J Physiol Renal Physiol.* 284, F3-F10; Doran et al., (2006) *Am J Physiol Regul Integr Comp Physiol.* 290, R1446-R1459; Klein et al., (2012) *Pflugers Arch.* 464, 561-572; Smith, C P. (2009) *Exper Physiol.* 94, 180-185; Stewart, G. (2011) *Br J Pharmacol.* 164, 1780-1792; Fenton et al., (2002) *Am J Physiol Renal Physiol.* 283, F817-F825; Fenton, R A. (2009) *Pflugers Arch.* 458, 169-177; Shayakul et al., (2013) *Mol Aspects Med.* 34, 313-322; Shayakul, C., and Hediger, M A. (2004) *Pflugers Arch.* 447, 603-609; Sands, J. M. (2004) *Curr Opin Nephrol Hypertens.* 13, 525-532).

Phenotype analysis of various UT-A (Fenton, et al., (2004) *Proc Natl Acad Sci USA.* 101, 7469-7474; Fenton et al., (2005) *J Am Soc Nephrol.* 16, 1583-1592; Fenton, R A. (2008) *Curr Opin Nephrol Hypertens.* 17, 513-518; Uchida et al. (2005) *Mol Cell Biol.* 25, 7357-7363; Klein, et al. (2013). *FASEB J* 27, 1111.17 (EB abstract)) and UT-B (see, e.g., Yang, et al., (2002) *J Biol Chem.* 277, 10633-10637) knockout mice, as well as mathematical modeling (see, e.g., Liu, et al., (2013) *Bioorgan Med Chem Lett.* 23, 3338-3341), indicate that UT-A1 in inner medullary collecting duct is the UT isoform whose inhibition is predicted to have the greatest diuretic action. The potential utility of UT inhibitors as novel, salt-sparing diuretics has been discussed in several recent reviews (see, e.g., Knepper, M. A., and Miranda, C. A. (2013) *Kidney Intern.* 83, 991-993; Sands, J. M. (2013) *Chem Biol.* 24, 1201-1202; Sands, J. M., and Layton, H. E. (2014) *Annu Rev Physiol.* 10, 387-409; Denton, J. S., Pao, A. C., and Maduke, M. (2013) *Am J Physiol Renal Physiol.* 305, F931-F942).

Until recently, the only UT inhibitors were chemical analogs of urea with millimolar potency (see, e.g., Mayrand et al. (1983) *J Gen Physiol.* 81, 221-237). A high-throughput screen was recently developed to identify UT-B inhibitors based on an erythrocyte lysis assay (see, e.g., Levin et al., (2007) *FASEB J.* 21, 551-563). UT-B inhibitors with low nanomolar $IC_{50}$ were identified and optimized, but produced only a mild reduction in maximum urinary concentrating function (see, e.g., Yao et al., (2012) *J Am Soc Nephrol.* 23, 1210-1220; Anderson et al., (2012) *J Med Chem.* 55, 5942-5950). Other studies reported diuretic effects in rats injected with high doses of a triazolothienopyrimidine (see, e.g., Li et al., (2013) *Kidney Internat.* 83, 1076-1086) or a urea analog (dimethylthiourea) (see, e.g., Cil et al. (2012) *Hum Exp Toxicol.* 31, 1050-1055), though the inhibition selectivity and pharmacology of these compounds were not determined. More recently, recognizing the greater predicted diuretic efficacy of UT-A versus UT-B inhibition, a cell-based fluorescence screen was developed to identify UT-A inhibitors, which produced compounds with high UT-A selectivity and others that inhibited both UT-A and UT-B (see, e.g., Esteva-Font et al., (2013) *Chem Biol.* 20, 1235-1244). However, the unfavorable metabolic stability and solubility of the original UT-A inhibitors precluded their testing in animal models.

Urea transport (UT) proteins of the UT-A class are expressed in epithelial cells in kidney tubules where they are required for the formation of concentrated urine by countercurrent multiplication. Five UT-A urea transporter isoforms (UT-A1, UT-A2, UT-A3, UT-A4, and UT-A5) are encoded by alternatively splicing of the Slc14A2 gene (see, e.g., Bagnasco et al., *Am. J. Physiol. Renal Physiol.* 281: F400-F406 (2001); Shayakul et al., *Pflugers Arch.* 447:603-609 (2004); Bagnasco, *Pflugers Arch.* 450:217-26 (2005); Sands, *Curr. Opin. Nephrol. Hypertens.* 13:525-32 (2004); Bagnasco, *Am. J. Physiol. Renal Physiol.* 284:F3-F10 (2003); Sands et al. *Am. Physiol.* 273:F321-39 (1997); Sands, *Annu. Rev. Physiol.* 65:543-66 (2003)). The Slc14A1 gene encodes a single UT-B isoform (see, e.g., Sands, *Curr. Opin. Nephrol. Hypertens.* 13:525-32 (2004); Lucien et al., *J Biol. Chem.* 273:12973-80 (1998); Bagnasco, *Am. J Physiol. Renal Physiol.* 284:F3-F10 (2003); Sidoux et al., *J Biol. Chem.* 274:30228-35 (1999); see also e.g., Tsukaguchi et al., *J Clin Invest.* 99:1506-15 (1997)). Exemplary nucleotide sequences and the encoded polypeptide sequences may be found, for example, in GenBank Accession Nos. NM 007163.2 (UT-A); BC110445.1 (UT-A); BC110446.1 (UT-A); NM 007163.2 (UT-A); AF349446.1 (UT-A1); X96969.1 (UT-A2). The compounds described herein may inhibit at least one, at least two or more, UT-A isoforms, which include UT-A1, UT-A2, UT-A3, UT-A4, UT-A5, and UT-A6. In a particular embodiment, the compounds inhibit UT-A1.

As described herein, a small molecule screen identified compounds that selectively inhibited UT-A urea transport with low micromolar potency by a non-competitive inhibition mechanism. The screen was performed against isoform UT-A1, the rate-limiting urea transporter expressed on the luminal membrane of epithelial cells in kidney inner medullary collecting duct (see, e.g., Smith, C P. (2009) *Exper Physiol.* 94, 180-185). UT-A1 inhibitors probably also inhibit isoform UT-A3, which is expressed at the basolateral membrane in the same cells and is highly homologous to UT-A1, as UT-A1 consists of one UT-A3 and one UT-A2 molecule in tandem. Also, urinary concentrating ability was not impaired in UT-A1/A3 (double) knockout mice after transgenic replacement of UT-A1 (see, e.g., Klein et al. (2013) FASEB J27, 1111.17 (EB abstract)). The other renal UT-A isoform, UT-A2, is expressed in the thin descending limb of Henle's loop (see, e.g., Smith, C P. (2009) *Exper Physiol.* 94, 180-185), but appears to play a minimal role, as urinary concentrating function is unimpaired in UT-A2 knockout mice (see, e.g., Uchida et al. (2005) *Mol Cell Biol.* 25, 7357-7363). The relatively mild urinary concentrating defect in UT-B knockout mice (see, e.g., Yang et al. (2002) *J Biol Chem.* 277, 10633-10637) and in humans with loss of function mutations in UT-B (see, e.g., Lucien et al. (1998) *J Biol Chem.* 273, 12973-12980; Sands et al. (1992) *J Am Soc Nephrol.* 2, 1689-1696) suggests a much less important role for UT-B compared to UT-A isoforms in urinary concentrating function, which is supported here by the marked diuresis in rats produced by a UT-A1 selective inhibitor. Without wishing to be bound by theory, inhibition of urea transport in inner medullary collecting duct would prevent uptake of urea from luminal fluid into the medullary interstitium and hence reduce interstitial osmolality. Inhibition of UT-B, which impairs urea uptake from the interstitium into the renal microvasculature, is predicted to have minimal further effect when little urea is delivered to the interstitium with UT-A1 inhibition.

The two chemical classes described herein have drug-like properties, including the presence of multiple hydrogen bonding acceptors, favorable molecule weight, a Log P, and topological polar surface areas. The average molecular weights are 333 and 421 for the compounds of structures I and II, respectively; average a Log P values are 4.6 and 2.0, and average topological polar surface areas are 86 and 95 $Å^2$. These values are within the Lipinski (see, e.g., Lipinski, C. A., Lombardo, F., Dominy, B. W., Feeney, P. J. (2001) *Adv Drug Deliv Rev.* 46, 3-26) and Veber (see, e.g., Veber et al. (2002) *J Med Chem.* 45, 2615-2623) criteria for orally bioavailable drugs. Facile synthesis of these 2 compound classes, as shown in this study, will allow rapid preparation of targeted chemical analogs to improve inhibition activities and physicochemical properties.

In vitro functional studies indicated a non-competitive mechanism for $UTA_{inh}$-E02 and $UTA_{inh}$-F11 inhibition of urea transport. A cytoplasmic binding mode deduced by molecular docking was supported experimentally by the non-competitive inhibition mechanism and inhibitor membrane permeabilities. Notwithstanding the limitations of homology modeling of membrane transport proteins and of molecular docking computations, $UTA_{inh}$-E02 and $UTA1_{inh}$-F11 appear to be oriented in the pore region, with additional structural features positioned to interact with an outer hydrophobic pocket.

A high-throughput screen of synthetic small molecules, and optimization by structure-activity analysis, yielded selective, non-competitive inhibitors of UT-A urea transport that produced a strong diuretic response in rats, showing UT-A as a target for development of salt-sparing diuretics with a novel mechanism of action. Structure-activity analysis identified compounds that inhibited UT-A selectively by a non-competitive mechanism with $IC_{50}$ down to ~1 μM. Molecular modeling identified putative inhibitor binding sites on rat UT-A. Formulations and administration procedures were established to give therapeutic inhibitor concentrations in blood and urine in an art-accepted animal model. As described herein, intravenous administration of an indolethiazole or a γ-sultambenzosulfonamide compounds at 20 mg/kg increased urine output by 3-5-fold and reduced urine osmolality by ~2-fold compared to vehicle control rats, even under conditions of maximum antidiuresis produced by dDAVP. The diuresis was reversible and showed urea>salt excretion.

UT-blocking diuretics may have utility alone, or in combination with conventional salt transport-blocking diuretics, in edema due to fluid overload (e.g., associated with congestive heart failure, nephrotic syndrome and cirrhosis) and in hyponatremia due to chronic elevation in vasopressin (e.g., associated with syndrome of inappropriate antidiuretic hormone secretion (SIADH)). Because of their unique mechanism of action on renal countercurrent multiplication, UT-A1 inhibitors may be effective in states of refractory edema where conventional diuretics such as furosemide and thiazides have limited efficacy.

The following compounds and pharmaceutical compositions comprising these compounds that are urea transporter inhibitors may be useful for treating diseases, disorders, and conditions treatable by inhibiting UT-A transport of urea. In one embodiment, the compound is represented by Formula (I):

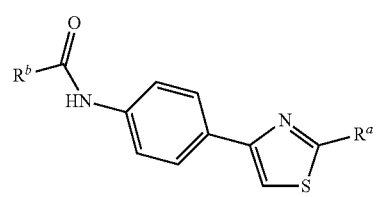

Formula (I)

wherein,
$R^a$ is aryl, heteroaryl, cycloalkyl, or heterocyclyl; and
$R^b$ is alkyl,
a stereoisomer, enantiomer or tautomer thereof, a pharmaceutically acceptable salt thereof, a pharmaceutical composition thereof or a prodrug thereof.

In more specific embodiments, $R^b$ is methyl or ethyl.

In one embodiment, $R^a$ is aryl. In another embodiment, $R^a$ is heteroaryl. In another embodiment, $R^a$ is cycloalkyl. In another embodiment, $R^a$ is heterocyclyl. In a more specific embodiment, $R^a$ is phenyl. In a more specific embodiment, $R^a$ is indolyl.

In one embodiment, $R^b$ is methyl. In another embodiment, $R^b$ is ethyl.

In another embodiment, the compound is represented by Formula (II):

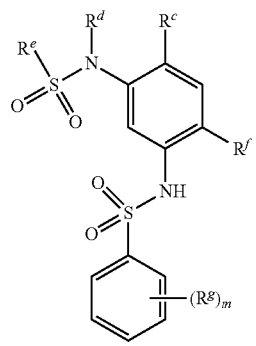

Formula (II)

wherein, m is 0, 1, 2 or 3;

$R^c$ is hydrogen, halo or alkyl; or $R^c$ and $R^d$, together with the C and N atoms to which they are attached respectively, form a 5-member or 6-member heterocyclyl ring;

$R^e$ is alkyl; or $R^e$ and $R^d$, together with the S and N atoms to which they are attached respectively, form a 5-member or 6-member heterocyclyl ring;

$R^f$ is hydrogen or alkoxy; and $R^g$ is independently, at each occurrence, alkyl, alkoxy, or halo, a stereoisomer, enantiomer or tautomer thereof, a pharmaceutically acceptable salt thereof, a pharmaceutical composition thereof or a prodrug thereof.

In one embodiment, $R^c$ is hydrogen. In another embodiment, $R^c$ is halo. In another embodiment, $R^c$ is $C_{1-3}$alkyl.

In another embodiment, $R^c$ and $R^d$, together with the C and N atoms to which they are attached respectively, form a 5-member heterocyclyl ring. In another embodiment, $R^c$ and $R^d$, together with the C and N atoms to which they are attached respectively, form a 6-member heterocyclyl ring.

In another embodiment, $R^e$ is $C_{1-3}$alkyl.

In one embodiment, $R^e$ and $R^d$, together with the S and N atoms to which they are attached respectively, form a 5-member heterocyclyl ring. In one embodiment, $R^e$ and $R^d$, together with the S and N atoms to which they are attached respectively, form a 6-member heterocyclyl ring.

In one embodiment, $R^f$ is hydrogen. In another embodiment, $R^f$ is $C_{1-3}$alkoxy.

In one embodiment, $R^g$ is $C_{1-3}$alkyl. In another embodiment, $R^g$ is $C_{1-3}$alkoxy. In another embodiment, $R^g$ is halo.

In a further embodiment, the compound is represented by Formula (IIa):

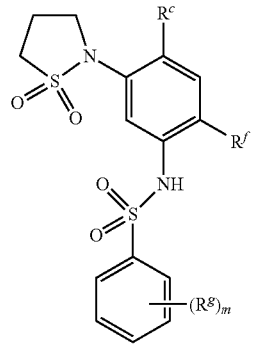

Formula (IIa)

wherein, m is 0, 1, 2 or 3;

$R^c$ is hydrogen, halo or $C_{1-3}$alkyl;

$R^f$ is hydrogen or $C_{1-3}$alkoxy; and $R^g$ is independently, at each occurrence, $C_{1-3}$alkyl, $C_{1-3}$alkoxy, or halo, a stereoisomer, enantiomer or tautomer thereof, a pharmaceutically acceptable salt thereof, a pharmaceutical composition thereof or a prodrug thereof.

In one embodiment, $R^c$ is hydrogen. In another embodiment, $R^c$ is halo. In another embodiment, $R^c$ is $C_{1-3}$alkyl. In another embodiment, $R^c$ is hydrogen. In another embodiment, $R^c$ is chloro.

In one embodiment, $R^f$ is hydrogen. In another embodiment, $R^f$ is $C_{1-3}$alkoxy. In another embodiment, $R^f$ is methoxy.

In one embodiment, $R^g$ is $C_{1-3}$alkyl. In another embodiment, $R^g$ is $C_{1-3}$alkoxy. In another embodiment, $R^g$ is halo. In one embodiment, $R^g$ is independently, at each occurrence, methyl, methoxy, fluoro or chloro. In another embodiment, $R^g$ is methyl. In another embodiment, $R^g$ is methoxy. In another embodiment, $R^g$ is fluoro. In another embodiment, $R^g$ is chloro.

In one embodiment, m is 2 or 3.

In another embodiment, the compound is represented by Formula (IIb):

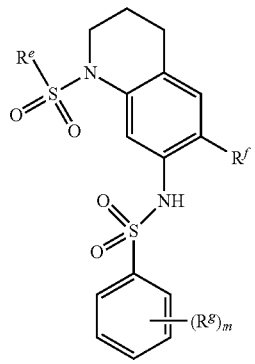

Formula (IIb)

wherein, m is 0, 1, 2 or 3;

$R^e$ is $C_{1-3}$alkyl;

$R^f$ is hydrogen or $C_{1-3}$alkoxy; and $R^g$ is independently, at each occurrence, $C_{1-3}$alkyl, $C_{1-3}$alkoxy, or halo, a stereoisomer, enantiomer or tautomer thereof, a pharmaceutically acceptable salt thereof, a pharmaceutical composition thereof or a prodrug thereof.

In one embodiment, $R^f$ is hydrogen. In another embodiment, $R^f$ is $C_{1-3}$alkoxy.

In one embodiment, $R^g$ is $C_{1-3}$alkyl. In another embodiment, $R^g$ is $C_{1-3}$alkoxy. In another embodiment, $R^g$ is halo.

In one embodiment, m is 0; $R^e$ is $C_{1-3}$alkyl; and $R^f$ is hydrogen.

In various embodiments, the compounds of structure I, II, IIa, and IIb are disclosed in Table 1. In other various embodiments, the compounds of structure I, II, IIa, and IIb suitable for the pharmaceutical compositions and methods described herein are those disclosed in Table 1.

As used herein, "alkyl" refers to a straight or branched hydrocarbon chain radical consisting solely of carbon and hydrogen atoms, containing no unsaturation, having from one to twelve carbon atoms ($C_{1-12}$alkyl), one to eight carbon atoms ($C_{1-8}$alkyl), or one to six carbon atoms ($C_{1-6}$alkyl), and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, and the like. $C_{1-3}$alkyl refers to an alkyl having 1-3 carbon chain atoms, e.g., methyl, ethyl, n-propyl, or isopropyl. Unless stated otherwise specifically in the specification, an alkyl group may be unsubstituted or substituted by one or more substituents, as defined herein.

"Alkoxy" refers to the radical —O-alkyl, wherein alkyl is as defined herein. $C_{1-3}$alkoxy refers to alkoxy having 1-3 carbon chain atoms, e.g., methoxy, ethoxy, and the like.

"Halo" refers to bromo, chloro, fluoro or iodo.

"Aryl" refers to a hydrocarbon ring system radical comprising hydrogen, 6 to 18 carbon atoms and at least one aromatic ring. For purposes of this invention, the aryl radical may be a monocyclic, bicyclic, tricyclic or tetracyclic ring system, which may include fused or bridged ring systems. Aryl radicals include, but are not limited to, phenyl. Unless stated otherwise specifically in the specification, an alkyl group may be unsubstituted or substituted by one or more substituents, as defined herein.

"Cycloalkyl" refers to a stable non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Unless stated otherwise specifically in the specification, an alkyl group may be unsubstituted or substituted by one or more substituents, as defined herein.

"Heteroaryl" refers to a 5- to 14-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. An example of heteroaryl is indolyl, indazolyl, isoindolyl, indolinyl, isoindolinyl, isoquinolyl, indolizinyl, isoxazolyl and the like. Unless stated otherwise specifically in the specification, an alkyl group may be unsubstituted or substituted by one or more substituents, as defined herein.

"Heterocyclyl" refers to a stable 3- to 18-membered non-aromatic ring radical which consists of two to twelve carbon atoms and from one to six heteroatoms selected from the group consisting of nitrogen, oxygen and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, thienyl[1,3]dithianyl, decahydroisoquinolyl, imidazolinyl, and the like. Unless stated otherwise specifically in the specification, an alkyl group may be unsubstituted or substituted by one or more substituents, as defined herein.

"Substituent" refers to alkyl, alkoxy, halo, haloalkyl (alkyl substituted with one or more halo), cyano (—CN), oxo (=O), nitro (—$NO_2$), aryl, cycloalkyl, heterocyclyl, heterocyclylalkyl, heteroaryl, —$R^{15}$—OR, —$R^1$—OC(O)—$R^{14}$, —$R^{15}$—N($R^{14}$)$_2$, —$R^{15}$—C(O)$R^{14}$, —$R^{15}$—C(O)O$R^{14}$, —$R^{15}$—C(O)N($R^{14}$)$_2$, —$R^{15}$—N($R^{14}$)C(O)O$R^{16}$, —$R^{15}$—N($R^{14}$)C(O)$R^{16}$, —$R^{15}$—N($R^{14}$)S(O)$_t R^{16}$ (where t is 1 to 2), —$R^{15}$—N=C(O$R^{14}$)$R^{14}$, —$R^{15}$—S(O)$_t$O$R^{16}$ (where t is 1 to 2), —$R^{15}$—S(O)$_p R^{16}$ (where p is 0 to 2), and —$R^{15}$—S(O)$_t$N($R^{14}$)$_2$ (where t is 1 to 2) where each $R^{14}$ is independently hydrogen, alkyl, haloalkyl, cycloalkyl, aryl, heterocyclyl, heteroaryl; each $R^{15}$ is independently a direct bond or a straight or branched alkylene or alkenylene chain; and each $R^{16}$ is hydrogen, alkyl, haloalkyl, cycloalkyl, aryl, heterocyclyl, heteroaryl.

The compounds described herein may generally be used as the free acid or free base. Alternatively, the compounds may be used in the form of acid or base addition salts. Acid addition salts of the free base amino compounds may be prepared according to methods well known in the art, and may be formed from organic and inorganic acids. Suitable organic acids include (but are not limited to) maleic, fumaric, benzoic, ascorbic, succinic, methanesulfonic, acetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include (but are not limited to) hydrochloric, hydrobromic, sulfuric, phosphoric, and nitric acids. Base addition salts of the free acid compounds of the compounds described herein may also be prepared by methods well known in the art, and may be formed from organic and inorganic bases. Suitable inorganic bases included (but are not limited to) the hydroxide or other salt of sodium, potassium, lithium, ammonium, calcium, magnesium, iron, zinc, copper, manganese, aluminum, and the like, and organic bases such as substituted ammonium salts. Thus, the term "pharmaceutically acceptable salt" of compounds of structures (I), (II), (IIa) and (IIb), and substructures thereof, as well as any and all substructures and specific compounds described herein is intended to encompass any and all pharmaceutically suitable salt forms.

Compounds of structures (I), (II), (IIa) and (IIb), and substructures thereof may sometimes be depicted as an anionic species. One of ordinary skill in the art will recognize that the compounds exist with an equimolar ratio of cation. For instance, the compounds described herein can exist in the fully protonated form, or in the form of a salt such as sodium, potassium, ammonium or in combination with any inorganic base as described above. When more than one anionic species is depicted, each anionic species may independently exist as either the protonated species or as the salt species. In some specific embodiments, the compounds described herein exist as the sodium salt.

Furthermore, some of the crystalline forms of any compound described herein may exist as polymorphs, which are also included and contemplated by the present disclosure. In addition, some of the compounds may form solvates with water or other organic solvents. Often crystallizations produce a solvate of the disclosed compounds. As used herein, the term "solvate" refers to an aggregate that comprises one or more molecules of any of the disclosed compounds with one or more molecules of solvent. The solvent may be water, in which case the solvate may be a hydrate. Alternatively, the solvent may be an organic solvent. Thus, the presently disclosed compounds may exist as a hydrate, including a monohydrate, dihydrate, hemihydrate, sesquihydrate, trihydrate, tetrahydrate and the like, as well as the corresponding solvated forms. Certain embodiments of the compounds may be true solvates, while in other cases, some embodiments of the compounds may merely retain adventitious water or be a mixture of water plus some adventitious solvent.

Specific and analogous reactants may also be identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs may be prepared by custom chemical synthesis houses, where many of the standard chemical supply houses (e.g., those listed above) provide custom synthesis services. A reference for the preparation and selection of pharmaceutical salts of the present disclosure is P. H. Stahl & C. G. Wermuth "Handbook of Pharmaceutical Salts," Verlag Helvetica Chimica Acta, Zurich, 2002.

With regard to stereoisomers, the compounds of structures (I), (II), (IIa) and (IIb), as well as any substructure herein, may have one or more chiral (or asymmetric) centers, and may thus give rise to enantiomers, diastereomers, and other stereoisomeric forms that may be defined, in terms of absolute stereochemistry, as (R)— or (S)—. When the compounds described herein contain olefinic double bonds or other centers of geometric asymmetry, and unless specified otherwise, it is intended that the compounds include both E and Z geometric isomers (e.g., cis or trans). Likewise, unless otherwise specified, all possible isomers, as well as their racemic and optically pure forms, and all tautomeric forms are also intended to be included. It is therefore contemplated that various stereoisomers and mixtures thereof and includes "enantiomers," which refers to two stereoisomers whose molecules are nonsuperimposeable mirror images of one another. Thus, the compounds may occur in any isomeric form, including racemates, racemic mixtures, and as individual enantiomers or diastereomers. A "tautomer" refers to a proton shift from one atom of a molecule to another atom of the same molecule. Some embodiments of the disclosed compounds include tautomers of any said compounds.

"Prodrug" is meant to indicate a compound that may be converted under physiological conditions or by solvolysis to a biologically active compound described herein. Thus, the term "prodrug" refers to a metabolic precursor of a compound described herein that is pharmaceutically acceptable. A prodrug may be inactive when administered to a subject in need thereof, but is converted in vivo to an active compound as described herein. Prodrugs are typically rapidly transformed in vivo to yield the parent compound described herein, for example, by hydrolysis in blood. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam). A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein.

The term "prodrug" is also meant to include any covalently bonded carriers which release the active compound as described herein in vivo when such prodrug is administered to a mammalian subject. Prodrugs of a compound described herein may be prepared by modifying functional groups present in the compound described herein in such a way that the modifications are cleaved, either in routine manipulation or in vivo, to the parent compound described herein. Prodrugs include compounds described herein wherein a hydroxy, amino or mercapto group is bonded to any group that, when the prodrug of the compound is administered to a mammalian subject, cleaves to form a free hydroxy, free amino or free mercapto group, respectively. Examples of prodrugs include, but are not limited to, ester and amide derivatives of hydroxy, carboxy, mercapto or amino functional groups in the compounds described herein and the like.

The compounds of structures (I), (II), (IIa) and (IIb) may be synthesized according to the methods described herein and that are readily practiced by a person skilled in the art. In general, the compounds used in the reactions described herein may be made according to organic synthesis techniques known to those skilled in this art, starting from commercially available chemicals and/or from compounds described in the chemical literature. "Commercially available chemicals" may be obtained from standard commercial sources including Acros Organics (Pittsburgh Pa.), Aldrich Chemical (Milwaukee Wis., including Sigma Chemical and Fluka), Apin Chemicals Ltd. (Milton Park UK), Avocado Research (Lancashire U.K.), BDH Inc. (Toronto, Canada), Bionet (Cornwall, U.K.), Chemservice Inc. (West Chester Pa.), Crescent Chemical Co. (Hauppauge N.Y.), Eastman Organic Chemicals, Eastman Kodak Company (Rochester N.Y.), Fisher Scientific Co. (Pittsburgh Pa.), Fisons Chemicals (Leicestershire UK), Frontier Scientific (Logan Utah), ICN Biomedicals, Inc. (Costa Mesa Calif.), Key Organics (Cornwall U.K.), Lancaster Synthesis (Windham N.H.), Maybridge Chemical Co. Ltd. (Cornwall U.K.), Parish Chemical Co. (Orem Utah), Pfaltz & Bauer, Inc. (Waterbury Conn.), Polyorganix (Houston Tex.), Pierce Chemical Co. (Rockford Ill.), Riedel de Haen AG (Hanover, Germany), Spectrum Quality Product, Inc. (New Brunswick, N.J.), TCI America (Portland Oreg.), Trans World Chemicals, Inc. (Rockville Md.), and Wako Chemicals USA, Inc. (Richmond Va.).

Methods known to one of ordinary skill in the art may be identified through various reference books and databases.

Suitable reference books and treatise that detail the synthesis of reactants useful in the preparation of compounds of the present disclosure, or provide references to articles that describe the preparation, include for example, "Synthetic Organic Chemistry," John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure," 4th Ed., Wiley-Interscience, New York, 1992. Additional suitable reference books and treatise that detail the synthesis of reactants useful in the preparation of compounds of the present disclosure, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Quin, L. D. et al. "A Guide to Organophosphorus Chemistry" (2000) Wiley-Interscience, ISBN: 0-471-31824-8; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

In other embodiments, provided herein are pharmaceutical compositions comprising at least one of the compounds of structures (I), (II), (IIa) and (IIb) described above and herein and a pharmaceutically acceptable (i.e., suitable) excipient.

In another embodiment, methods of using the compounds and pharmaceutical compositions comprising the compounds are provided herein. In one embodiment, a method is provided for treating a disease, disorder, or condition that is treatable by inhibiting transport of urea in a subject. This method comprises administering to the subject a pharmaceutical composition comprising a pharmaceutically acceptable excipient and at least one of the compounds of structure (I), (II), (IIa) and (IIb) described above and herein. In one embodiment, the disease, disorder, or condition to be treated by inhibiting transport of urea is selected from (a) refractory edema associated with cirrhosis, nephritic syndrome, acute renal failure, chronic renal insufficiency, or congestive heart failure; (b) syndrome of inappropriate antidiuretic hormone secretion (SIADH); (c) azotemia; (e) fluid retention; (f) hypertension, and (g) abnormal uresis. In another specific embodiment, the disease, disorder, or condition to be treated is associated with a fluid retention imbalance; in another certain specific embodiment, the fluid retention imbalance comprises urea clearance insufficiency. In still another embodiment, treating the disease, disorder, or condition comprises inhibiting the capability of at least one urea transporter to transport urea. In certain specific embodiments, the at least one urea transporter is a UT-B transporter.

In other embodiments, methods are provided for inhibiting transport of urea across a cell membrane comprising contacting a cell with a composition that comprises at least one of the compounds of structure (I), (II), (IIa) and (IIb) (including substructures and specific compounds) described herein, wherein the cell comprises at least one urea transporter. In one embodiment, at least one compound described herein inhibits the capability of a UT-B transporter to transport urea.

As described herein the aforementioned compounds of structure (I), (II), (IIa) and (IIb) are capable of inhibiting the transport activity a urea transporter (e.g., UT-A) and are therefore useful for treating a disease, disorder, or condition treatable by inhibiting transport of urea. These compounds are potent inhibitors that selectively and reversibly inhibit urea transport via UT-A thereby reducing urinary concentration in a subject to whom the compound is administered.

Inhibition of Urea Transport

Provided herein are methods for using the compounds of structure (I), (II), (IIa) and (IIb), and substructures and specific compounds described herein. As described in detail herein, methods are provided for treating a disease, disorder, or condition treatable by inhibiting transport of a neutrally charged solute (e.g., urea) in a subject by administering to the subject in need thereof a pharmaceutical composition comprising at least one of the compounds of structure (I), (II), (IIa) and (IIb), and substructures and specific compounds described above. In a particular embodiment, the compounds and compositions described herein may treat a disease, disorder, or condition by inhibiting transport of urea by a urea transporter. The compound may specifically inhibit all urea transporters or may interact with and inhibit only one subfamily of urea transporter (i e.g., UT-A transporters).

The compounds of the structure (I), (II), (IIa) and (IIb), and substructures and compounds described herein may be used to alter (i.e., increase or decrease in a statistically significant or biologically significant manner) transport of urea across a cell membrane by at least one urea transporter. In particular embodiments, transport activity of at least one urea transporter is inhibited by a compound of structure (I), (II), (IIa) and (IIb), and substructures and compounds, thus the compounds are capable of preventing, blocking, or decreasing transport of urea across a cell membrane. Methods are provided for an in vitro assay in which a cell comprising at least one urea transporter is contacted (combined, mixed, or in some manner permitted to interact) with a composition comprising at least one compound of structure (I), (II), (IIa) and (IIb). In one embodiment, at least one compound described herein inhibits transport of urea by a UT-A transporter. In certain embodiments, the cell is a renal cell, a brain cell, a red blood cell, or a testis cell. In a particular embodiment, the cell is a renal cell.

Urea transporters (UTs) are transmembrane proteins that transport urea across cellular membranes. UTs may be expressed in such tissues as the outer and inner medulla of the kidney, erythropoietic tissue, testis and hepatocytes. One function of UTs is production of concentrated urea, which is critical for retention of water.

In one embodiment, methods are provided for decreasing in a statistically significant or biologically significant manner transport of urea across a cell membrane by a urea transporter in a cell. Such methods comprise contacting (i.e., combining, mixing or in some manner permitting interaction with) the cell and any one or more (i.e., at least one) of the compounds of structure (I), (II), (IIa) and (IIb), and substructures described herein or a composition comprising at least one or more of such compounds. The compounds described herein are capable of inhibiting transport of urea by at least one urea transporter-A (e.g., a UT-A1) in a cell in vivo (i.e., in an animal, including a human) or in vitro in an assay method, for example.

In a specific embodiment, a method is provided for inhibiting transport of urea across a cell membrane, which method comprises contacting (i.e., combining, mixing or in some manner permitting interaction with) a cell with at least one compounds of the structure (I), (II), (IIa) and (IIb), and substructures or composition comprising such a compound as described herein, wherein the cell comprises at least one urea transporter, particularly a UT-A transporter (e.g., UT-A1). The compounds described herein inhibit (i.e., reduce, abrogate, prevent, or decrease in a statistically significant or biologically significant manner) the capability of at least one UT-A to transport urea across a cell membrane.

The transporter may be endogenously expressed by the cell (i.e., the genome of the cell comprises a nucleotide sequence that encodes the transporter, which is transcribed into mRNA that is translated). Alternative, for example, with respect to in vitro assay methods, the transporter may be recombinantly expressed in the cell (i.e., the cell comprises an exogenous polynucleotide that directs the expression of the transporter polypeptide).

With respect to assay methods described herein for characterizing a compound as an inhibitor of UT-A, cells may be obtained or derived from a biological sample. A biological sample as used herein refers in certain embodiments to a sample containing at least one cell or a plurality of cells that endogenously or exogenously expresses at least one urea transporter. A biological sample may be a blood sample, such as whole blood or a cellular fraction of whole blood, biopsy specimen, body fluids that contain cells that express at least one transporter (e.g., lung lavage, ascites, mucosal washings, synovial fluid), bone marrow, lymph nodes, tissue explant, organ culture, or any other tissue or cell preparation from a subject or a biological source. A sample may further refer to a tissue or cell preparation in which the morphological integrity or physical state of the tissue has been disrupted, for example, by dissection, dissociation, solubilization, fractionation, homogenization, biochemical or chemical extraction. The subject or biological source may be a human or non-human animal, a primary cell culture (e.g., kidney cells or other cells that endogenously express a transporter), or culture adapted cell line, including but not limited to, genetically engineered cell lines that may contain chromosomally integrated or episomal recombinant nucleic acid sequences, immortalized or immortalizable cell lines, somatic cell hybrid cell lines, differentiated or differentiatable cell lines, transformed cell lines, and the like.

The cells comprising a urea transporter that is inhibited by the compounds and compositions described herein include cells that endogenously express a urea transporter polypeptide. Exemplary cells that endogenously express a urea transporter include but are not limited to a renal cell, a brain cell, a red blood cell, a liver cell, or a testis cell. Transport of urea by urea transporters and transport of water by aquaporins are opposing processes in such cells. An exemplary cell that may be used in the methods described herein and that expresses a urea transporter is a red blood cell (i.e., erythrocyte).

Alternatively, the cells (which may be any one of a renal cell, a brain cell, a red blood cell, a liver cell, or a testis cell or other cell) may comprise an exogenous polynucleotide that encodes a urea transporter polypeptide. The cell may be transfected, transformed, or transduced with a recombinant expression vector, which comprises a polynucleotide that is capable of directing expression of at least one urea transporter. To direct expression of at least one transporter, the polynucleotide comprises a nucleotide sequence that encodes at least one urea transporter, which nucleotide sequence is operatively linked to at least one expression control sequence (e.g., a promoter, enhancer, transcriptional control element, and the like). Recombinant expression vectors may be prepared according to methods and techniques with which a person skilled in the molecular biology art is familiar. An exemplary cell line that may be transfected with a recombinant expression vector comprising a polynucleotide that directs expression of a urea transporter or other transport includes Madin-Darby canine kidney cells (MDCK).

Cells may be obtained or derived from any one of a number of animals, including mammals. Mammalian cells may be obtained or may have originated from humans; non-human primates; rodents such as mice, rats, or rabbits; cats (feline); dogs (canine); cattle (bovine); sheep (ovine); pigs (porcine); llamas; and camels, for example.

Methods that may be used to identify and to characterize urea transporter inhibitors, such as the compounds described herein, include those described herein and routinely practiced in the art. Such assays may be used to determine the effective concentrations of a particular compound and thus are useful for predicting the capability of the compound to effectively treat a disease, disorder, or condition treatable by inhibiting urea transporter activity in a subject.

A person skilled in the art will appreciate that the methods and techniques described herein may include appropriate control samples to evaluate and ensure the robustness, accuracy, and precision of the method. Statistical methods may be applied to the determinations of the particular assay in the absence and presence of a candidate agent to evaluate and compare the different candidate agents tested.

Treatment of Urea Clearance Disorders

A composition comprising at least one of the compounds of structure (I), (II), (IIa) and (IIb) described herein may be used for treating a disease, disorder, or condition in a subject. In one embodiment, methods are provided for treating a disease, disorder, or condition that is treatable by inhibiting transport of urea wherein the method comprises administering a composition comprising at least one compound as described herein.

UT inhibitors have a fundamentally different mechanism-of-action from conventional diuretics, which target kidney tubule salt transporters, and so may act in synergy. Diuretics are used widely to increase renal salt and water excretion in fluid overload conditions such as congestive heart failure, cirrhosis and nephrotic syndrome, and when vasopressin levels are inappropriately high, such as in syndrome of inappropriate secretion of antidiuretic hormone (SIADH). By disrupting countercurrent mechanisms, UT inhibitors alone or in combination with loop diuretics, may induce a diuresis in states of refractory edema where conventional diuretics are not effective (see, e.g., Zhang *Am J Physiol Renal Physiol* 285: F731-F747 (2003); Fenton et al., *Pflugers Arch* 458:169-177, (2009); Smith, *Exp Physiol* 94:180-185 (2009)).

A disease, condition, or disorder treatable by inhibiting transport of urea includes a fluid retention imbalance, for example, urea clearance insufficiency. In certain instances, the urea clearance insufficiency is a renal urea clearance insufficiency. The compounds described herein (i.e., compounds of structures (I), (II), (IIa) and (IIb) and substructures thereof) may be useful for therapy of diuretic-refractory edema in heart and liver failure. These compounds may be used to treat a refractory edema associated with or caused by a cardiovascular, renal, or metabolic disease, disorder, or condition, such as cirrhosis, nephritic syndrome, acute renal failure, chronic renal insufficiency, and congestive heart failure. In certain other embodiments, the disease, disorder, or condition to be treated is syndrome of inappropriate antidiuretic hormone secretion (SIADH), azotemia, hypertension, fluid retention, and abnormal uresis. In other certain embodiments, at least one of the compounds described herein may also be used in combination with a loop diuretic.

In a particular embodiment, methods are provided for treating such a disease, disorder, or condition by inhibiting the capability of at least one UT-A to transport urea. In one embodiment, at least one of the compounds described herein inhibits the capability of at least the UT-A1 transporter to transport urea. A compound described herein may be used as a type of diuretic, an "urearetic," that affects renal urea clearance mechanisms.

Methods are also provided for using the compounds of structure (I), (II), (IIa) and (IIb) for treating a disease, disorder, or condition treatable by inhibiting transport of urea in a subject by administering to the subject in need thereof a pharmaceutical composition comprising at least one of the compounds having the structure and substructures described above. The disease, disorder, or condition that may be treated using the compounds and compositions described herein may be associated with a fluid retention imbalance such as urea clearance insufficiency. Urea is a by-product of protein metabolism that is formed in the liver. Because urea contains ammonia, which is toxic to an animal body, urea must be quickly filtered from the blood by the kidneys and excreted in the urine. Conservation of water in mammals depends significantly on the transport of urea, particularly in the kidney. Urea is generated as the major end product of hepatic nitrogen metabolism and is excreted primarily by the kidney. In a particular embodiment the disease, disorder, or condition to be treated is renal urea clearance insufficiency.

As understood by a person skilled in the medical art, the terms, "treat" and "treatment," refer to medical management of a disease, disorder, or condition of a subject (i.e., patient) (see, e.g., Stedman's Medical Dictionary). In general, an appropriate dose and treatment regimen provide at least one compound of structures (I), (II), (IIa) and (IIb), and substructures described herein in an amount sufficient to provide therapeutic and/or prophylactic benefit. Therapeutic and/or prophylactic benefit includes, for example, an improved clinical outcome, both therapeutic treatment and prophylactic or preventative measures, wherein the object is to prevent or slow or retard (lessen) an undesired physiological change or disorder, or to prevent or slow or retard (lessen) the expansion or severity of such disorder. As discussed herein, beneficial or desired clinical results from treating a subject include, but are not limited to, abatement, lessening, or alleviation of symptoms that result from or are associated the disease, condition, or disorder to be treated; decreased occurrence of symptoms; improved quality of life; longer disease-free status (i.e., decreasing the likelihood or the propensity that a subject will present symptoms on the basis of which a diagnosis of a disease is made); diminishment of extent of disease; stabilized (i.e., not worsening) state of disease; delay or slowing of disease progression; amelioration or palliation of the disease state; and remission (whether partial or total), whether detectable or undetectable; and/or overall survival. "Treatment" can also mean prolonging survival when compared to expected survival if a subject were not receiving treatment. Subjects in need of treatment include those who already have the condition or disorder as well as subjects prone to have or at risk of developing the disease, condition, or disorder, and those in which the disease, condition, or disorder is to be prevented (i.e., decreasing the likelihood of occurrence of the disease, disorder, or condition).

In particular embodiments of the methods described herein, the subject is a human or non-human animal. A subject in need of the treatments described herein may exhibit symptoms or sequelae of a disease, disorder, or condition described herein or may be at risk of developing the disease, disorder, or condition. Non-human animals that may be treated include mammals, for example, non-human primates (e.g., monkey, chimpanzee, gorilla, and the like), rodents (e.g., rats, mice, gerbils, hamsters, ferrets, rabbits), lagomorphs, swine (e.g., pig, miniature pig), equine, dogs (canine); cats (feline), cattle (bovine); sheep (ovine); pigs (porcine); llamas; and camels; and other domestic, farm, and zoo animals.

In one embodiment, treating any one of the aforementioned diseases or conditions comprises inhibiting (i.e., preventing, decreasing, reducing, abrogating, or inhibiting in a statistically significant or biologically significant manner) the capability of at least one urea transporter (e.g., UT-A) to transport urea by administering a composition comprising any one or more of the compounds of the structure (I), (II), (IIa) and (IIb), and substructures. The subject, and thus the source of the urea transporter, may be a human or non-human mammal.

To evaluate and to monitor the effectiveness of any one of the compounds described herein to treat a disease, disorder, or condition, one or more of several clinical assay methods may be performed that are familiar to a person skilled in the clinical art. For example, a clinical method called a urea clearance test may be performed. By way of example, a blood sample is obtained from a subject to whom the compound is being administered so that the amount of urea in the bloodstream can be determined. In addition, a first urine sample may be collected from the subject and additional samples may be collected over time (for example, at least one hour later). The amount of urea quantified in the urine indicates the amount of urea that is filtered, or cleared by the kidneys into the urine. Another clinical assay method measures urine osmolality (i.e., the amount of dissolved solute particles in the urine). Inability of the kidneys to concentrate the urine in response to restricted fluid intake, or to dilute the urine in response to increased fluid intake during osmolality testing may indicate decreased kidney function.

Urea is a by-product of protein metabolism and is formed in the liver. Urea is then filtered from the blood and excreted in the urine by the kidneys. The BUN (blood urea nitrogen) test measures the amount of nitrogen contained in the urea. High BUN levels may indicate kidney dysfunction, but because blood urea nitrogen is also affected by protein intake and liver function, the test is usually performed in conjunction with determination of blood creatinine, which is considered a more specific indicator of kidney function. Low clearance values for creatinine and urea indicate diminished ability of the kidneys to filter these waste products from the blood and excrete them in the urine. As clearance levels decrease, blood levels of creatinine and urea nitrogen increase. An abnormally elevated blood creatinine, a more specific and sensitive indicator of kidney disease than the BUN, is diagnostic of impaired kidney function.

Pharmaceutical Compositions

Also provided herein are pharmaceutical compositions that comprise any one or more of the compounds of structures (I), (II), (IIa) and (IIb) (and substructures and specific structures thereof). The compounds described herein may be formulated in a pharmaceutical composition for use in treatment or preventive (or prophylactic) treatment (e.g., reducing the likelihood of occurrence or exacerbation of disease or of one or more symptoms of the disease).

As used herein, a subject may be any mammal, including a human, that may have or be afflicted with a disease, condition, or disorder described herein. A pharmaceutical composition may be a sterile aqueous or non-aqueous solution, suspension or emulsion, which additionally comprises at least one physiologically acceptable excipient (i.e., a physiologically and pharmaceutically suitable non-toxic and inactive material or ingredient that does not interfere with the activity of the active ingredient; an excipient also may be called a carrier). Such compositions may be in the form of a solid, liquid, or gas (aerosol). Alternatively, compositions described herein may be formulated as a lyophilizate, or compounds may be encapsulated within liposomes using technology known in the art. Pharmaceutical compositions may also contain other components, which may be biologically active or inactive. Such components include, but are not limited to, buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, stabilizers, dyes, flavoring agents, and suspending agents and/or preservatives.

In pharmaceutical dosage forms, any one or more of the compounds of structure (I), (II), (IIa) and (IIb), and substructures, and specific structures described herein may be administered in the form of a pharmaceutically acceptable derivative, such as a salt, or they may also be used alone or in appropriate association, as well as in combination, with other pharmaceutically active compounds. The methods and excipients described herein are exemplary and are in no way limiting. An effective amount or therapeutically effective amount refers to an amount of a compound or a composition comprising one or more compounds that when administered to a subject, either as a single dose or as part of a series of doses, is effective to produce a desired therapeutic effect.

Optimal doses may generally be determined using experimental models and/or clinical trials. The optimal dose may depend upon the body mass, weight, or blood volume of the subject. In general, the amount of a compound described herein, that is present in a dose, ranges from about 0.01 µg to about 1000 µg per kg weight of the host or from about 1 mg to about 1000 mg per kg weight of the host. In other embodiments, the dose ranges between about 1-30 mg/kg weight of host (e.g., 1 mg, 2 mg, 4 mg, 5 mg, 6 mg, 7 mg, 8 mg, 9 mg or about 10 mg or about 15 mg or about 20 mg per kg or about 25 mg or about 30 mg per kg weight of the host). The use of the minimum dose that is sufficient to provide effective therapy is usually preferred. Subjects may generally be monitored for therapeutic effectiveness using assays suitable for the condition being treated or prevented, which assays will be familiar to those having ordinary skill in the art and some of which are described herein. The level of a compound that is administered to a subject may be monitored by determining the level of the compound in a biological fluid, for example, in the blood, blood fraction (e.g., serum, plasma), and/or in the urine, and/or other biological sample from the subject. Any method practiced in the art to detect the compound may be used to measure the level of compound during the course of a therapeutic regimen.

The dose of a composition comprising at least one of the compounds described herein for treating a disease or condition may depend upon the subject's condition, that is, stage of the disease, severity of symptoms caused by the disease, general health status, as well as age, gender, and weight, and other factors apparent to a person skilled in the medical art. Similarly, the dose of the compound for treating a disease or disorder treatable by inhibiting urea transporters as described herein may be determined according to parameters understood by a person skilled in the medical art.

Pharmaceutical compositions comprising at least one compound of structure (I), (II), (IIa) and (IIb) may be administered in a manner appropriate to the disease or disorder to be treated as determined by persons skilled in the medical arts. An appropriate dose and a suitable duration and frequency of administration will be determined by such factors as the condition of the patient, the type and severity of the patient's disease, the particular form of the active ingredient, and the method of administration. In general, an appropriate dose (or effective dose) and treatment regimen provides the composition(s) comprising at least one compound as described herein in an amount sufficient to provide therapeutic and/or prophylactic benefit (for example, an improved clinical outcome, such as more frequent complete or partial remissions, or longer disease-free and/or overall survival, or a lessening of symptom severity or other benefit as described in detail above).

The pharmaceutical compositions described herein that comprise at least one of the compounds of structure (I), (II), (IIa) and (IIb) may be administered to a subject in need by any one of several routes that effectively deliver an effective amount of the compound. Such administrative routes include, for example, oral, parenteral, enteral, rectal, intranasal, buccal, sublingual, intramuscular, and transdermal. Compositions administered by these routes of administration and others are described in greater detail herein.

A pharmaceutical composition may be a sterile aqueous or non-aqueous solution, suspension or emulsion, which additionally comprises a physiologically acceptable excipient (pharmaceutically acceptable or suitable excipient or carrier) (i.e., a non-toxic material that does not interfere with the activity of the active ingredient). Such compositions may be in the form of a solid, liquid, or gas (aerosol). Alternatively, compositions described herein may be formulated as a lyophilizate, or compounds may be encapsulated within liposomes using technology known in the art. Pharmaceutical compositions may also contain other components, which may be biologically active or inactive. Such components include, but are not limited to, buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, stabilizers, dyes, flavoring agents, and suspending agents and/or preservatives.

Any suitable excipient or carrier known to those of ordinary skill in the art for use in pharmaceutical compositions may be employed in the compositions described herein. Excipients for therapeutic use are well known, and are described, for example, in Remington: The Science and Practice of Pharmacy (Gennaro, 21$^{st}$ Ed. Mack Pub. Co., Easton, Pa. (2005)). In general, the type of excipient is selected based on the mode of administration, as well as the chemical composition of the active ingredient(s). Pharmaceutical compositions may be formulated for any appropriate manner of administration, including, for example, topical, oral, nasal, intrathecal, rectal, vaginal, intraocular, subconjunctival, sublingual or parenteral administration, including subcutaneous, intravenous, intramuscular, intrasternal, intracavernous, intrameatal or intraurethral injection or infusion. For parenteral administration, the carrier preferably comprises water, saline, alcohol, a fat, a wax or a buffer. For oral administration, any of the above excipients or a solid excipient or carrier, such as mannitol, lactose, starch, magnesium stearate, sodium saccharine, talcum, cellulose, kaolin, glycerin, starch dextrins, sodium alginate, carboxymethylcellulose, ethyl cellulose, glucose, sucrose and/or magnesium carbonate, may be employed.

A pharmaceutical composition (e.g., for oral administration or delivery by injection) may be in the form of a liquid. A liquid pharmaceutical composition may include, for example, one or more of the following: a sterile diluent such as water for injection, saline solution, preferably physiological saline, Ringer's solution, isotonic sodium chloride, fixed oils that may serve as the solvent or suspending medium, polyethylene glycols, glycerin, propylene glycol or other solvents; antibacterial agents; antioxidants; chelating agents; buffers and agents for the adjustment of tonicity such as sodium chloride or dextrose. A parenteral preparation can be enclosed in ampoules, disposable syringes or multiple dose vials made of glass or plastic. The use of physiological saline is preferred, and an injectable pharmaceutical composition is preferably sterile.

A composition comprising any one of the compounds of structure (I), (II), (IIa) and (IIb) may be formulated for sustained or slow release. Such compositions may generally be prepared using well known technology and administered by, for example, oral, rectal or subcutaneous implantation, or by implantation at the desired target site. Sustained-release formulations may contain the compound dispersed in a carrier matrix and/or contained within a reservoir surrounded by a rate controlling membrane. Excipients for use within such formulations are biocompatible, and may also be biodegradable; preferably the formulation provides a relatively constant level of active component release. The amount of active compound contained within a sustained release formulation depends upon the site of implantation, the rate and expected duration of release, and the nature of the condition to be treated or prevented.

For oral formulations, at least one of the compounds described herein can be used alone or in combination with appropriate additives to make tablets, powders, granules or capsules, for example, with conventional additives, such as lactose, mannitol, corn starch or potato starch; with binders, such as starch, gelatin, natural sugars such as glucose or beta-lactose, corn sweeteners, natural and synthetic gums such as acacia, tragacanth, or sodium alginate, carboxymethylcellulose, polyethylene glycol, waxes, crystalline cellulose, cellulose derivatives, and acacia; with disintegrators, such as corn starch, potato starch or sodium carboxymethylcellulose, methyl cellulose, agar, bentonite, or xanthan gum; with lubricants, such as talc, sodium oleate, magnesium stearate sodium stearate, sodium benzoate, sodium acetate, or sodium chloride; and if desired, with diluents, buffering agents, moistening agents, preservatives, coloring agents, and flavoring agents. The compounds may be formulated with a buffering agent to provide for protection of the compound from low pH of the gastric environment and/or an enteric coating. A compound included in the compositions may be formulated for oral delivery with a flavoring agent, e.g., in a liquid, solid or semi-solid formulation and/or with an enteric coating.

Oral formulations may be provided as gelatin capsules, which may contain the active compound along with powdered carriers, such as lactose, starch, cellulose derivatives, magnesium stearate, stearic acid, and the like. Similar carriers and diluents may be used to make compressed tablets. Tablets and capsules can be manufactured as sustained release products to provide for continuous release of active ingredients over a period of time. Compressed tablets can be sugar coated or film coated to mask any unpleasant taste and protect the tablet from the atmosphere, or enteric coated for selective disintegration in the gastrointestinal tract. Liquid dosage forms for oral administration may contain coloring and/or flavoring agents to increase acceptance of the compound by the subject.

A composition comprising any one of the compounds of structure (I), (II), (IIa) and (IIb) may be formulated for sustained or slow release. Such compositions may generally be prepared using well known technology and administered by, for example, oral, rectal or subcutaneous implantation, or by implantation at the desired target site. Sustained-release formulations may contain the compound dispersed in a carrier matrix and/or contained within a reservoir surrounded by a rate controlling membrane. Excipients for use within such formulations are biocompatible, and may also be biodegradable; preferably the formulation provides a relatively constant level of active component release. The amount of active compound contained within a sustained release formulation depends upon the site of implantation, the rate and expected duration of release, and the nature of the condition to be treated or prevented.

The compounds of structure (I), (II), (IIa) and (IIb) described herein can be formulated in pharmaceutical compositions as suppositories by mixing with a variety of bases such as emulsifying bases or water-soluble bases. These compounds may be administered rectally via a suppository. The suppository can include vehicles such as cocoa butter, carbowaxes and polyethylene glycols, which melt at body temperature, yet are solidified at room temperature.

The compounds of structure (I), (II), (IIa) and (IIb) may be used in aerosol formulation to be administered via inhalation. The compounds may be formulated into pressurized acceptable propellants such as dichlorodifluoromethane, propane, nitrogen and the like.

Any one or more of the compounds of structure (I), (II), (IIa) and (IIb) may be administered topically (e.g., by transdermal administration). Topical formulations may be in the form of a transdermal patch, ointment, paste, lotion, cream, gel, and the like. Topical formulations may include one or more of a penetrating agent, thickener, diluent, emulsifier, dispersing aid, or binder. When a compound is formulated for transdermal delivery, the compound may be formulated with or for use with a penetration enhancer. Penetration enhancers, which include chemical penetration enhancers and physical penetration enhancers, facilitate delivery of the compound through the skin, and may also be referred to as "permeation enhancers" interchangeably. Physical penetration enhancers include, for example, electrophoretic techniques such as iontophoresis, use of ultrasound (or "phonophoresis"), and the like. Chemical penetration enhancers are agents administered either prior to, with, or immediately following compound administration, which increase the permeability of the skin, particularly the stratum corneum, to provide for enhanced penetration of the drug through the skin. Additional chemical and physical penetration enhancers are described in, for example, Transdermal Delivery of Drugs, A. F. Kydonieus (ED) 1987 CRL Press; Percutaneous Penetration Enhancers, eds. Smith et al. (CRC Press, 1995); Lenneruas et al., *J. Pharm. Pharmacol.* 2002; 54(4):499-508; Karande et al., *Pharm. Res.* 2002; 19(5): 655-60; Vaddi et al., *Int. J. Pharm.* 2002 July; 91(7):1639-51; Ventura et al., *J. Drug Target* 2001; 9(5):379-93; Shokri et al., *Int. J. Pharm.* 2001; 228(1-2):99-107; Suzuki et al., *Biol. Pharm. Bull.* 2001; 24(6):698-700; Alberti et al., *J. Control Release* 2001; 71(3):319-27; Goldstein et al., *Urology* 2001; 57(2):301-5; Kiijavainen et al., *Eur. J. Pharm. Sci.* 2000; 10(2):97-102; and Tenjarla et al., *Int. J Pharm.* 1999; 192(2):147-58.

When a compound of structure (I), (II), (IIa) and (IIb) is formulated with a chemical penetration enhancer, the penetration enhancer is selected for compatibility with the compound, and is present in an amount sufficient to facilitate delivery of the compound through skin of a subject, e.g., for delivery of the compound to the systemic circulation. A compound of structure (I), (II), (IIa) and (IIb) may be provided in a drug delivery patch, e.g., a transmucosal or transdermal patch, and can be formulated with a penetration enhancer. The patch generally includes a backing layer, which is impermeable to the compound and other formulation components, a matrix in contact with one side of the backing layer, which matrix provides for sustained release, which may be controlled release, of the compound, and an adhesive layer, which is on the same side of the backing layer as the matrix. The matrix can be selected as is suitable for the route of administration, and can be, for example, a polymeric or hydrogel matrix.

Kits with unit doses of one or more of the compounds described herein, usually in oral or injectable doses, are provided. Such kits may include a container containing the unit dose, an informational package insert describing the use and attendant benefits of the drugs in treating pathological condition of interest, and optionally an appliance or device for delivery of the composition.

Also provided herein are methods of manufacturing the pharmaceutical compositions described herein that comprise at least one of the compounds of structure (I), (II), (IIa) and (IIb). In one embodiment, the method of manufacture comprises synthesis of the compound. Synthesis of one of more of the compounds described herein may be performed according to methods described herein and practiced in the art. In another method of manufacture, the method comprises comprise formulating (i.e., combining, mixing) at least one of the compounds disclosed herein with a pharmaceutically suitable excipient. These methods are performed under conditions that permit formulation and/or maintenance of the desired state (i.e., liquid or solid, for example) of each of the compound and excipient. A method of manufacture may comprise one or more of the steps of synthesizing the at least one compound of structure (I), (II), (IIa) and (IIb), formulating the compound with at least one pharmaceutically suitable excipient to form a pharmaceutical composition, and dispensing the formulated pharmaceutical composition in an appropriate vessel (i.e., a vessel appropriate for storage and/or distribution of the pharmaceutical composition).

Other embodiments and uses will be apparent to one skilled in the art in light of the present disclosures. The following examples are provided merely as illustrative of various embodiments and shall not be construed to limit the claims in any way.

EXAMPLES

Example 1

High-Throughput Screening

Primary screening was done using a collection of 50,000 chemically diverse, drug-like compounds from ChemDiv (San Diego, Calif.). For analysis of structure-activity relationships, >300 commercially available analogs (ChemDiv and Asinex, Winston-Salem, N.C.) were tested. Cells were plated on black 96-well Costar microplates with clear plastic bottoms (Corning, Corning, N.Y.) at 15,000 cells/well and cultured for 24 h at 37° C. before assay. Microplates containing cultured cells were washed twice with PBS and 150 µL of test compound (25 µM final) in PBS was added. Eighty wells contained test compounds, and the first and last columns of each plate contained negative (dimethyl sulfoxide, DMSO) and positive (0.35 mM phloretin) controls. The assays were done on a plate reader (Tecan Trading AG, Switzerland) equipped with a custom YFP filter set. Each assay consisted of a continuous 15-s read (5 Hz) in which 50 µL of 3.2 M urea in PBS was injected at 1 s (at 130 µL/s) to give a 800 mM final urea gradient.

Example 2

Compound Synthesis Procedures

All purchased materials and reagents were used without further purification. Flash chromatography was done with silica gel columns. $^1$H and $^{13}$C NMR spectra were obtained in chloroform ($CDCl_3$), dimethyl sulfoxide ($DMSO-d_6$) or methanol ($CD_3OD$) using a 300 MHz Varian spectrometer referenced to TMS. Chemical shifts are expressed in units of Hertz (Hz). Splitting patterns are designated as s (singlet), d (doublet), t (triplet), and m (multiplet). Mass spectrometry was done using a Waters LC/MS instrument (Waters Micromass ZQ with HPLC Waters 2695). LC was done on an XTERRA MS C18 column (2.1 mm×100 mm, 3.5 µm) with 0.2 mL/min water/acetonitrile (containing 0.1% formic acid), 16 min linear gradient, 5 to 95% acetonitrile. UV absorbance was detected at 254 nm.

N-(4-(2-(1H-indol-3-yl)thiazol-4-yl)phenyl)acetamide ($UTA_{inh}$-E02)

A mixture of 1H-indole-3-carbothioamide 1 (50 mg) and 4-acetaminophenacyl bromide 2 (61 mg) in 1 mL ethanol (EtOH) was refluxed for 2.5 h. Volatiles were then removed in vacuo, diluted with ethyl acetate (EtOAc) and washed with water and dried over anhydrous sodium sulfate ($Na_2SO_4$). The drying agent was removed by filtration and the solvent was evaporated under reduced pressure to yield a beige colored solid, which was purified using flash chromatography to yield $UTA_{inh}$-E02 (35 mg, 45%) as a white solid. Molecular formula: $C_{19}H_{15}N_3OS$; MS (ES+) (m/z) [M+1]$^+$ 334; $^1$H NMR (300 MHz, $CD_3OD$): δ 8.25-8.29 (2H, m), 7.98 (H, s), 7.96 (2H, s), 7.64-7.67 (2H, m), 7.50 (H, s), 7.46-7.49 (H, m), 7.23-7.27 (2H, m), 2.16 (3H, s); $^{13}$C NMR (75 MHz, $CD_3OD$): δ 170.2, 164.0, 154.4, 138.2, 136.9, 130.6, 126.5, 125.3, 124.6, 122.3, 120.5, 120.0, 119.8, 111.5, 111.1, 108.9, 22.7.

3-Chloro-N-(2-chloro-5-nitrophenyl)propane-1-sulfonamide (4)

To a solution of 2-chloro-5-nitroaniline 3 (600 mg, 3.48 mmol) in dichloromethane (7 mL) was added 3-chloropropanesulfonyl chloride (0.47 mL, 3.82 mmol) and pyridine (2.81 mL, 34.8 mmol). The reaction mixture was stirred at room temperature for 4 h then diluted with EtOAc and washed with water. The organic layer was separated and dried over $Na_2SO_4$. The drying agent was filtered and the solvent was evaporated under reduced pressure. The product was recrystallized with EtOH/acetonitrile to afford yellowish solid 4 (750 mg, 69%). Molecular formula: $C_9H_{10}Cl_2N2O_4S$; MS (ES+) (m/z) [M+1]$^+$ 313; $^1$H NMR (300 MHz, $CD_3OD$): δ 8.25-8.29 (2H, m), 7.98 (H, s), 7.96 (2H, s), 7.64-7.67 (2H, m), 7.50 (H, s), 7.23-7.27 (2H, m), 2.16 (3H, s).

2-(2-Chloro-5-nitrophenyl)-1,2-thiazolidine 1,1-dioxide (5)

To a solution of 4 (750 mg, 2.39 mmol) in acetonitrile (20 mL) was added potassium carbonate (826 mg, 5.99 mmol) and stirred overnight. The reaction mixture was diluted with water and extracted with EtOAc. The organic layer was washed with brine and dried over $Na_2SO_4$. The drying agent was filtered and solvent was evaporated under reduced pressure. The product was recrystallized with EtOH/acetonitrile to afford yellowish solid 5 (430 mg, 66%). Molecular formula: $C_9H_9ClN_2O_4S$; MS (ES+) (m/z) [M+1]$^+$ 277; $^1$H-NMR (300 MHz, $CD_3OD$): δ 8.48 (H, dd, J=0.3, 2.7 Hz), 8.25 (H, dd, J=2.7, 8.8 Hz), 7.82 (H, d, J=8.8 Hz), 3.85 (2H, t, J=6.7 Hz), 3.33 (2H, t, J=7.0 Hz), 2.58-2.63 (2H, m).

4-Chloro-3-(1,1-dioxide-, 2-thiazolidin-2-yl)aniline (6)

To a solution of 5 (60 mg, 0.18 mmol) in ethanol (2 mL) was added Pd/C on activated charcoal and the solution was bubbled with hydrogen gas overnight. The product was filtered on a Celite pad and the solvent was evaporated under reduced pressure, giving 6 (50 mg, 93%) as a white solid. Molecular formula: $C_9H_{11}ClN_2O_2S$ MS (ES+) (m/z) [M+1]$^+$ 247; $^1$H NMR (300 MHz, $CD_3OD$): δ 7.43 (H, d, J=8.0 Hz), 7.29 (H, br), 7.05 (H, d, J=7.7 Hz), 3.95 (2H, t, J=6.7 Hz), 3.61 (2H, t, J=7.0 Hz), 2.55 (2H, m).

N-[4-Chloro-3-(1,1-dioxido-1,2-thiazolidin-2-yl) phenyl]-2-methoxy-5-methylbenzene-sulfonamide (UTA$_{inh}$-F11)

To a solution of aniline 6 (40 mg, 0.16 mmol) in pyridine (1 mL) was added 6-methoxy-m-toluenesulfonyl chloride (36 mg, 0.16 mmol) and stirred at 60° C. for 2 h. The reaction mixture was diluted with water and the product was extracted with EtOAc. The organic layer was separated and dried over $Na_2SO_4$. The drying agent was filtered and the solvent was evaporated under reduced pressure. The product was recrystallized with EtOH/acetonitrile to afford UTA$_{inh}$-F11 (49 mg, 70%) as a white solid. Molecular formula: $C_{17}H_{19}ClN_2O_5S_2$; MS (ES+) (m/z) [M+1]$^+$ 431; $^1$H NMR (300 MHz, DMSO-d$_6$): δ 10.29 (H, s), 7.60-7.61 (2H, m), 7.35-7.41 (3H, m), 7.03-7.10 (2H, m), 3.81 (3H, s), 3.56 (2H, t, J=6.7 Hz), 3.38 (2H, t, J=Hz), 2.39 (2H, t, J=7.6 Hz), 2.25 (3H, s); $^{13}$C NMR (75 MHz, DMSO-d$_6$): δ154.7, 138.3, 136.0, 135.2, 131.1, 131.0, 129.7, 127.6, 125.8, 120.7, 120.3, 113.2, 56.6, 49.0, 47.1, 20.2, 19.4.

Example 3

Homology Modeling and Docking Computations

A homology model of rat UT-A1 was generated using the SWISS MODEL online utility (http://swissmodel.expasy-.org) (see, e.g., Arnold et al. (2006) *Bioinformatics* 22, 195-201; Bordoli, et al. (2009) *Nat Prot.* 4, 1-13) in automated mode, using the rat UT-A1 sequence (Accession No. NP_062220.2). The model was generated using coordinates from the X-ray crystal structure of bovine UT-B bound to selenourea (PDB=4EZC, solved to 2.5 Å) (see, e.g., Levin et al. (2012) *Proc Natl Acad Sci USA.* 109, 11194-11199) as a homology template. Two structural models were generated, comprising residues 105-449 (65.2% identity with bovine UT-B) and 568-909 of UT-A1 (67.5% sequence identity with bovine UT-B). Due to the slightly improved sequence identity, the latter model was used for docking computations. Because the UT-B template structure was solved as a homotrimer, the homology model was also generated in this format, and thus a single structure of the UT-A1 model was isolated for docking computations. The homology model for UT-A1 was prepared for docking using the FRED-RECEPTOR utility (Version 2.2.5, OpenEye Scientific, Santa Fe, N. Mex., at Internet site eyesopen[dot]com), with cytoplasmic and extracellular domains defined with 10 cubic Å boxes. An analogous homology model of rat UT-B was prepared in a similar fashion using SWISS MODEL, with the sequence of full rat UT-B protein (accession code, P97689). Structures of small molecule inhibitors were drawn in ChemDraw (Cambridge Software, Cambridge, Mass.), converted to SMILES strings, transformed to three-dimensional conformations, and minimized using PIPELINE PILOT (Accelrys, San Diego, Calif.). The single conformations were passed through MOLCHARGE (Version 1.5.0, OpenEye Scientific, Santa Fe, N. Mex., at Internet site eyesopen[dot]com) to apply MMFF charges (see, e.g., Halgren, T. A. (1996) *J Comp Chem.* 17, 490-519) and through OMEGA (Version 2.4.6, OpenEye Scientific, Santa Fe, N. Mex.) to generate multi-conformational libraries (see, e.g., Hawkins and Nicholls (2012) *J Chem Inf Model* 52, 2919-2936). The inhibitor conformational libraries were docked using FRED (Version 2.2.5, OpenEye Scientific, Santa Fe, N. Mex.) (see, e.g., McGann, M. (2012) *J. Comput Aided Mol.* 26, 897-906) which was configured to use consensus scoring, using the scoring functions ChemGauss3, ChemScore, OEChemScore, ScreenScore, ShapeGauss, PLP, and Zap-Bind. Docking of the inhibitors was carried out free of pharmacophore restraint. The final protein-inhibitor complexes were visualized using PYMOL (Schrödinger, San Diego, Calif.).

Example 4—Biological Methods

1. Cell Culture

MDCK cells stably expressing rat UT-A1 (see, e.g., Frohlich et al. (2006) *Am J Physiol Cell Physiol.* 291, C600-D606), YFP-H148Q/V163 S (see, e.g., Galietta, et al. (2001) *FEBS Lett.* 499, 220-224) and human AQP1, as described previously (see, e.g., Esteva-Font et al. (2013) *Chem Biol.* 20, 1235-1244), were grown in Dulbecco's modified Eagle medium (DMEM) containing 10% fetal bovine serum (FBS), penicillin G (100 U/mL), streptomycin (100 μg/mL), zeocin (500 μg/mL), geneticin (600 μg/mL) and Hygromycin (500 μg/mL) at 37° C., 5% $CO_2$. A Cell Clone with bright YFP fluorescence and relatively low AQP1 expression was used for the screen to maximize dynamic range.

2. Rats

Rats (Wistar males, 250-300 g) were purchased from Charles River Laboratories (Wilmington, Mass.). Rats were used for pharmacokinetic and diuretic studies. Procedures described below were approved by the Committee on Animal Research at the University of California, San Francisco.

3. In Vitro Functional Studies

Reversibility of UT-A1 inhibition was tested by preincubating MDCK cells expressing rat UT-A1, YFP-H148Q/V163S and AQP1 with inhibitors for 15 min (at 3 µM) and then washing the cells with PBS prior to assay. The urea concentration-dependence of UT-A1 inhibition was studied from inhibitor concentration-response data using different of urea gradients at zero initial intracellular urea concentration, or after preincubation of cells with different concentrations of urea for 10 min prior to a 1,600 mM urea gradient. The kinetics of UT-A1 inhibition was measured by adding inhibitors (3 µM) at different time points (0 to 10 min) prior to assay.

4. UT-B Inhibition Measurements

As described (see, e.g., Levin et al. (2007) *FASEB J.* 21, 551-563), whole rat blood was diluted to a hematocrit of ~1.5% in PBS containing 1.25 M acetamide and 5 mM glucose. Erythrocyte suspensions (100 µL) were added to 96-well round-bottom microplates and test compounds (1 µL) were added. After 15 min incubation, 20 µL of the erythrocyte suspension was added rapidly to each well containing 180 µL of PBS. Following vigorous mixing, erythrocyte lysis was quantified by absorbance at 710 nm. Non-lysed controls (isosmolar buffer) and lysed controls (0.7 mM phloretin) were added in each plate as negative and positive controls, respectively. Percentage erythrocyte lysis was computed as: % lysis=100% $(A_{neg}-A_{test})/(A_{neg}-A_{pos})$, where A is absorbance at 710 nm.

5. Transepithelial Transport Measurements

UT-A1 expressing MDCK cells were grown on 12-mm diameter collagen-coated Transwell inserts (0.4 µm pore size; Costar, Costar, N.Y.) to form tight monolayers (resistance>500 $\Omega cm^2$), as described (see, e.g., Levin et al. (2007) *FASEB J.* 21, 551-563). Urea flux in the basolateral-to-apical direction was measured in response to a 15 mM urea gradient in which PBS containing forskolin (10 µM), with or without UT-A1 inhibitor and 0.7 mM phloretin, was added to both the apical-facing (0.2 mL) and basal-facing (2 mL) surfaces. After 30 min the basal-facing solution was replaced by PBS containing test compound+15 mM urea. Apical fluid samples (5 µL) were collected at specified times for enzymatic assay of urea (QUANTICHROME Urea Assay Kit; BioAssay Systems, Hayward, Calif.). To measure inhibitor permeability across MDCK cell layers, compounds (20 µM) were added on the basal-facing surface and fluid samples (20 µL) from the apical-facing surface were collected at different time points and analyzed by LC/MS.

6. In Vitro Metabolic Stability

As described (see, e.g., Snyder et al. (2011) *J Med Chem.* 54, 5468-5477), compounds (each 5 µM) were incubated for specified times at 37° C. with rat liver microsomes (1 mg protein/mL; Sigma-Aldrich, St. Louis, Mo.) in potassium phosphate buffer (100 mM) containing 1 mM NADPH. The mixture was then chilled on ice, and 0.5 mL of ice-cold EtOAc was added. Samples were centrifuged for 15 min at 3,000 rpm, the supernatant evaporated to dryness, and the residue was dissolved in 100 µl mobile phase (acetonitrile: water [3:1], containing 0.1% formic acid) for LC/MS. Reverse-phase HPLC separations were carried out using a XTERRA MS C18 column (2.1 mm×100 mm, 3.5 m) equipped with a solvent delivery system (Waters model 2695, Milford, Mass.). The solvent system consisted of a linear gradient from 5 to 95% acetonitrile containing 0.1% formic acid, run over 16 min (0.2 mL/min flow rate).

7. Cell Toxicity and Off-Target Effects

MDCK cells on black 96-well Costar microplates with clear plastic bottoms were cultured for 24 h at 37° C. and incubated with test compounds (0 to 25 µM) for 24 h. Cell viability was assayed using AlamarBlue (Pierce, Rockford, Ill.) in which the reagent was added to each well, incubated for 30 min, and absorbance measured at 590 nm. For short-circuit current measurement, snapwell inserts containing MDCK cells were mounted on Ussing chambers. Test compounds (20 µM) were incubated with MDCK cells at both apical and basolateral sides for 10 min at 37° C. prior to addition of 20 µM forskolin and then 100 µM ATP. The apical and basolateral chambers contained identical solutions: 120 mM NaCl, 5 mM KCl, 1 mM $MgCl_2$, 1 mM $CaCl_2$, 5 mM HEPES, 25 mM $NaHCO_3$ and 10 mM glucose. Solutions were bubbled with 5% $CO_2$/95% $O_2$ and maintained at 37° C. Hemichambers were connected to a DVC-1000 voltage clamp (World Precision Instruments Inc., Sarasota, Fla.) via Ag/AgCl electrodes and 1 M KCl agar bridges for current recording.

8. Pharmacokinetics $UTA_{inh}$-E02 or $UTA_{inh}$-F11 was administered at 20 mg/kg intravenously by tail vein to rats. $UTA_{inh}$-E02 was formulated as a 5 mg/mL saline solution containing 20% dimethylacetamide and 40% 2-hydroxypropyl γ-cyclodextrin; $UTA_{inh}$-F11 was formulated as a 5 mg/mL saline solution containing 20% dimethylacetamide and 0.6 mg/mL NaOH. Blood samples were collected from the tail vein into K3EDTA mini collecting tubes (Greiner, Kremsmunster, Austria) at specified time points. Plasma samples were separated by centrifugation and kept frozen at −20 OC until analysis. Urine samples were also collected. Calibration standards were prepared in urine and plasma from control (non-treated) rats to which known amounts of $UTA_{inh}$-E02 or $UTA_{inh}$-F11 were added. The mixture was centrifuged for 20 min at 13,200 rpm and 90 µL of supernatant was taken for LC/MS. The solvent system consisted of a linear gradient from 5% to 95% acetonitrile containing 0.1% formic acid over 16 min (0.2 mL/min flow). Mass spectra was acquired on a mass spectrometer (Waters 2695+micromass ZQ; Waters) using electrospray (+) ionization, mass ranging from 100 to 1500 Da, 40-V cone voltage.

9. Diuretic Studies in Rats

Compound effects on urine output, osmolality and urea concentration were investigated in two conditions. Rats were placed in metabolic cages with water and food available ad libitum and spontaneously voided urine was collected for 3 h. Rats were then injected intravenously with 20 mg/kg $UTA_{inh}$-E02 or $UTA_{inh}$-F11 in formulations listed above (or vehicle alone), and returned to the metabolic cages without access to water, but free access to food. Spontaneously voided urine was collected every 3 h for a 6-h period. In some experiments, rats were administered dDAVP (4 µg/kg, IP) just before compound (or vehicle) injection and 3 h later. Rats did not have access to water, but had free access to food in dDAVP experiments. Urine osmolality was measured in water-diluted urine samples by freezing-point osmometry (Micro-osmometer; Precision Systems, Natick, Mass.). Urea concentration was determined by a colorimetric enzymatic assay as described above.

Example 5

UT-A1 Inhibitors Identified in a Small Molecule Screen

In order to identify UT-A inhibitors suitable for testing in rats, a collection of 50,000 synthetic small molecules was screened. As diagrammed in FIG. 1A (top), the fluorescence cell-based screen utilized MDCK cells stably rat expressing UT-A1, water channel AQP1 and the cytoplasmic chloride-sensing fluorescent protein YFP-H148Q/V163S. As described and validated previously (see, e.g., Esteva-Font et al. (2013) *Chem Biol.* 20, 1235-1244), extracellular addition of urea results in osmotic water efflux and cell shrinking, which increases intracellular chloride concentration and reduces YFP fluorescence. Urea entry results in increasing YFP fluorescence as cells re-swell. Inhibitors of UT-A1 urea transport produce a lesser reduction in fluorescence and slowed recovery. FIG. 1A (bottom) shows concentration-dependence data for two active compounds identified in the primary screen, with positive (non-selective UT inhibitor phloretin) and negative (vehicle) controls.

Figure 1B:
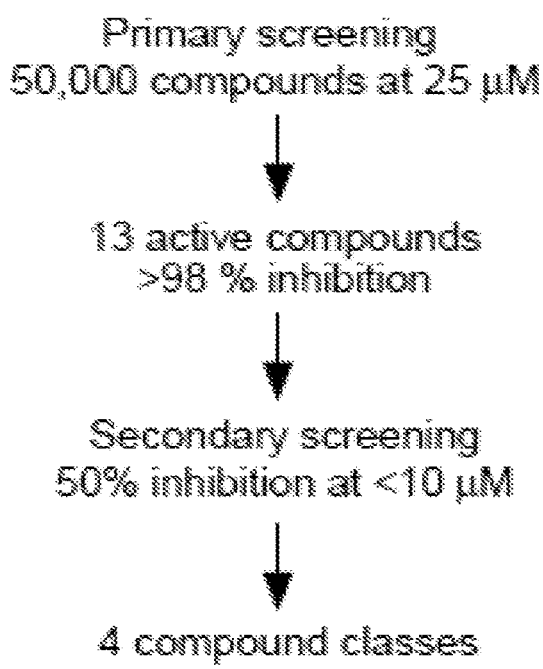
Figure 1C:
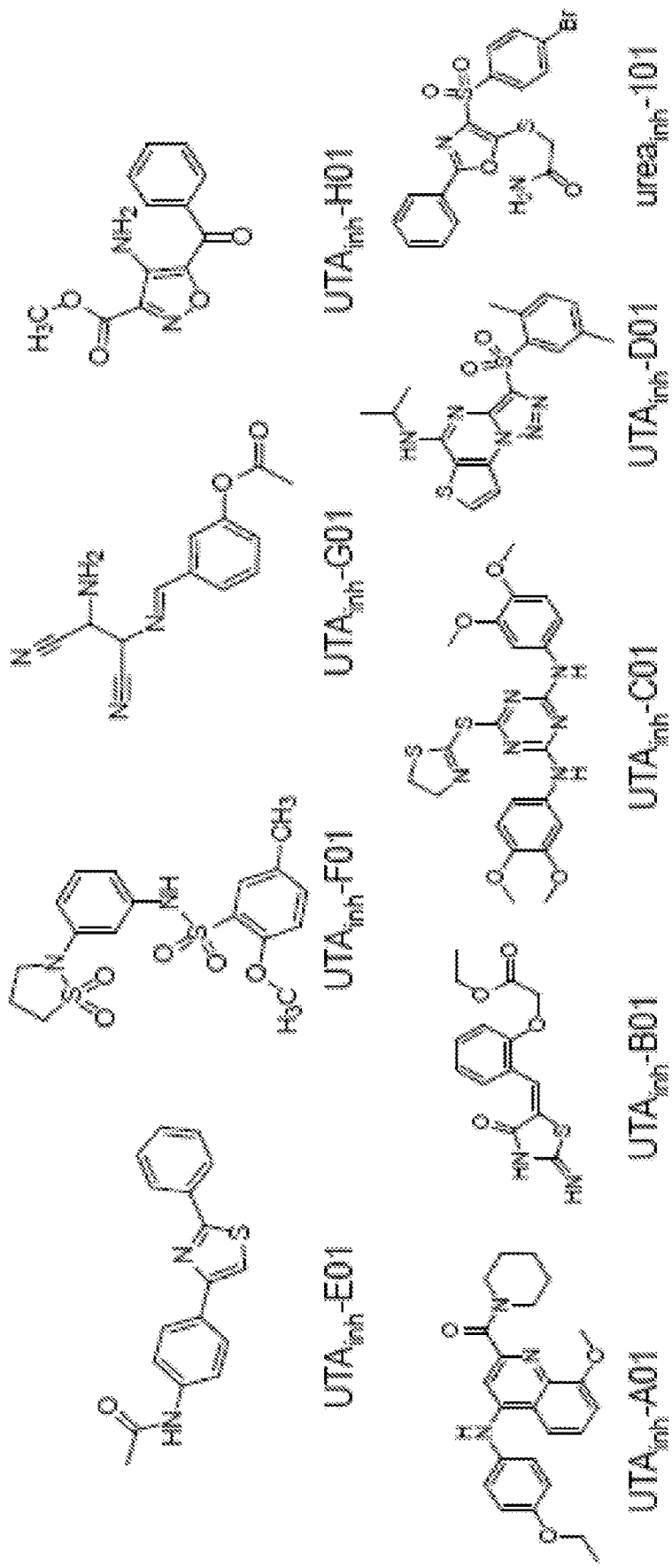

The primary screen produced 13 compounds giving >98% UT-A1 inhibition at 25 µM, with compounds of four distinct chemical scaffolds having $IC_{50}$<10 µM (FIG. 1B). FIG. 1C shows chemical structures of four classes of verified UT-A1 inhibitors identified in the screen: an arylthiazole ($UTA_{inh}$-E01), γ-sultambenzosulfonamide ($UTA_{inh}$-F01), aminocarbonitrilebutene ($UTA_{inh}$-G01) and 4-isoxazolamide ($UTA_{inh}$-H01). These four chemical scaffolds are different from previously reported urea transport inhibitors, whose structures are shown for comparison.

In summary, four chemical classes of UT-A1 inhibitors were identified, two of which were tested in rats and found to produce a marked diuresis. Functional studies and homology/docking computations suggested putative inhibitor binding sites on the intracellular-facing surface of the UT-A1 protein.

Example 6

Structure-Activity Analysis of UT-A1 Inhibitors

Figure 2A:
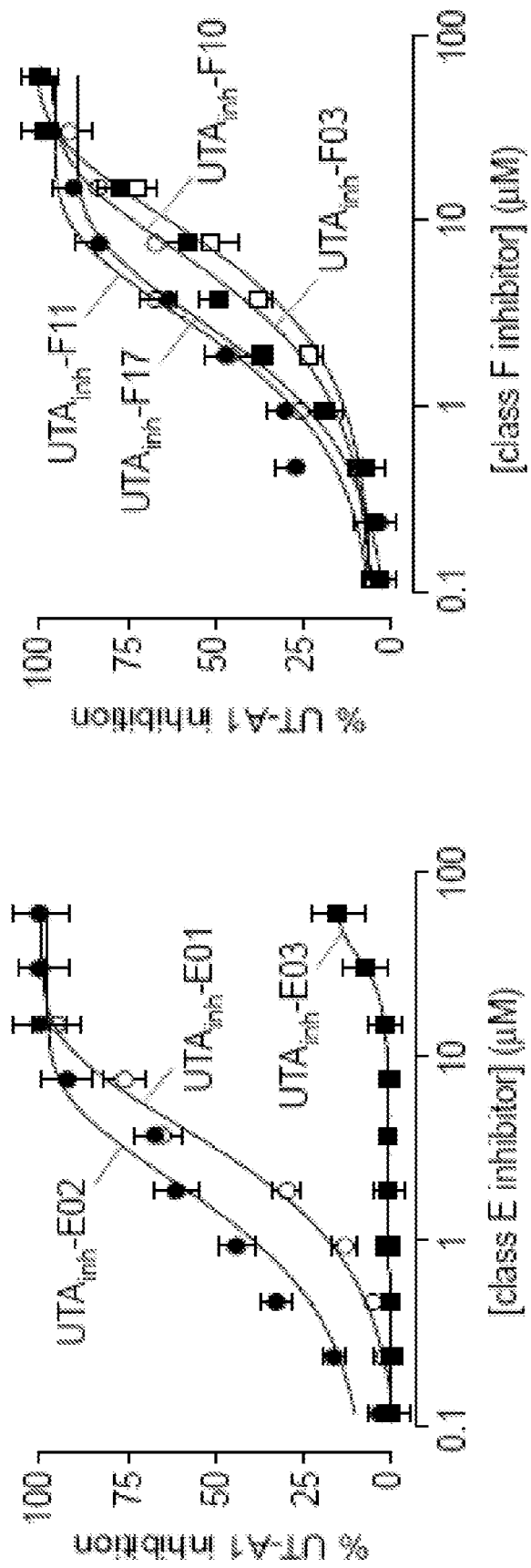
FIGS. 2A-2D presents structure-activity analysis of UT-A inhibitors.
Figure 2B:
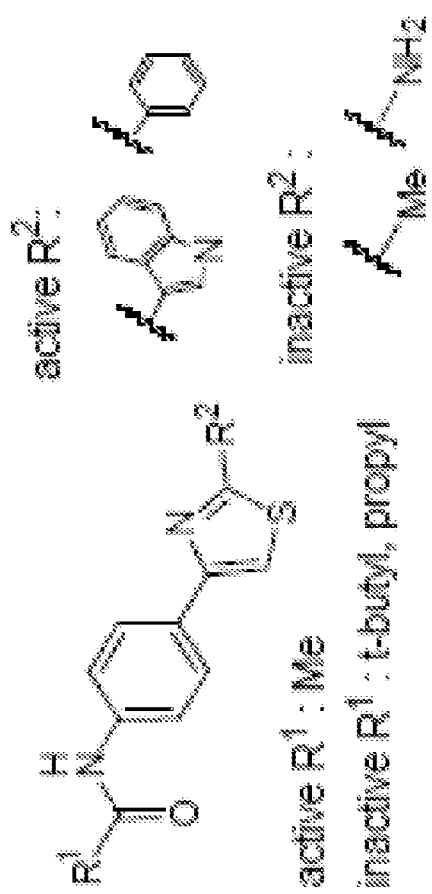
Figure 2C:
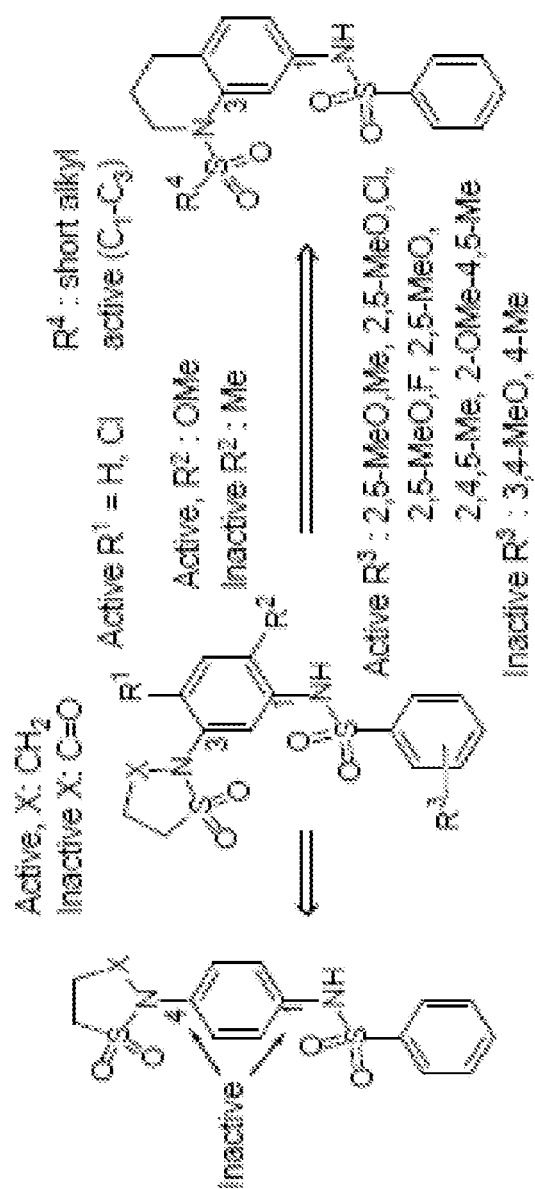

Of the inhibitor classes shown in FIG. 1C, two chemical classes, E and F (nomenclature $UTA_{inh}$-Exx and $UTA_{inh}$-Fxx), were found to have suitable metabolic stability and pharmacokinetics in rats (see below). FIG. 2A show concentration-inhibition data of representative class E and F compounds. A small set of 50 commercially available class E analogs were tested, with the best compound being 2-indole-4-aniline-thiazole ($UTA_{inh}$-E02) with $IC_{50}$~1 µM. Preliminary SAR analysis (FIG. 2B) showed that an acetamide group on the aniline ring and a thiazole was best, while larger alkyl amides reduced UT-A1 inhibition. SAR analysis of 200 commercially available class F analogs gave 20 compounds that produced >99% UT-A1 inhibition at M. The most potent compounds, $UTA_{inh}$-F01, -F09, -F11 and -F17, gave similar $IC_{50}$~1-2.5 µM. Several class F compounds also inhibited the other major UT isoform, UT-B (see below). Table 1 summarizes inhibition data for active class E and F compounds. The key structural determinants of class F compounds for UT-A1 inhibition activity, as deduced from the compounds listed in Table 1 and many inactive analogs, are summarized in FIG. 2C. Class F compounds are 1,3-diaminobenzenes with a benzosulfonamide group and a 5-member γ-sultam cyclic ring attached on the 1- and 3-amino positions, respectively ($UTA_{inh}$-F01 to F13). Analogs based on the 1,4-diaminobenzene ring were inactive, as was a 5-oxo group on the γ-sultam ring. Of note, analogs with the sultam endocyclically attached to 1,3-diaminobenzene are active ($UTA_{inh}$-F14 to F20). Further substitutions on the 1,3-diaminobenzene ring affected activity: 4-chloro and 6-methoxy ($UTA_{inh}$-F01, -F09, -F11) were tolerated, while 6-methyl group reduced activity ($UTA_{inh}$-F05 versus -F08). Di-substituted benzosulfonamide gave good activity, with the 2-methoxy-5-methyl substituent giving best UT-A1 inhibition ($UTA_{inh}$-F01, -F17).

Figure 2D:
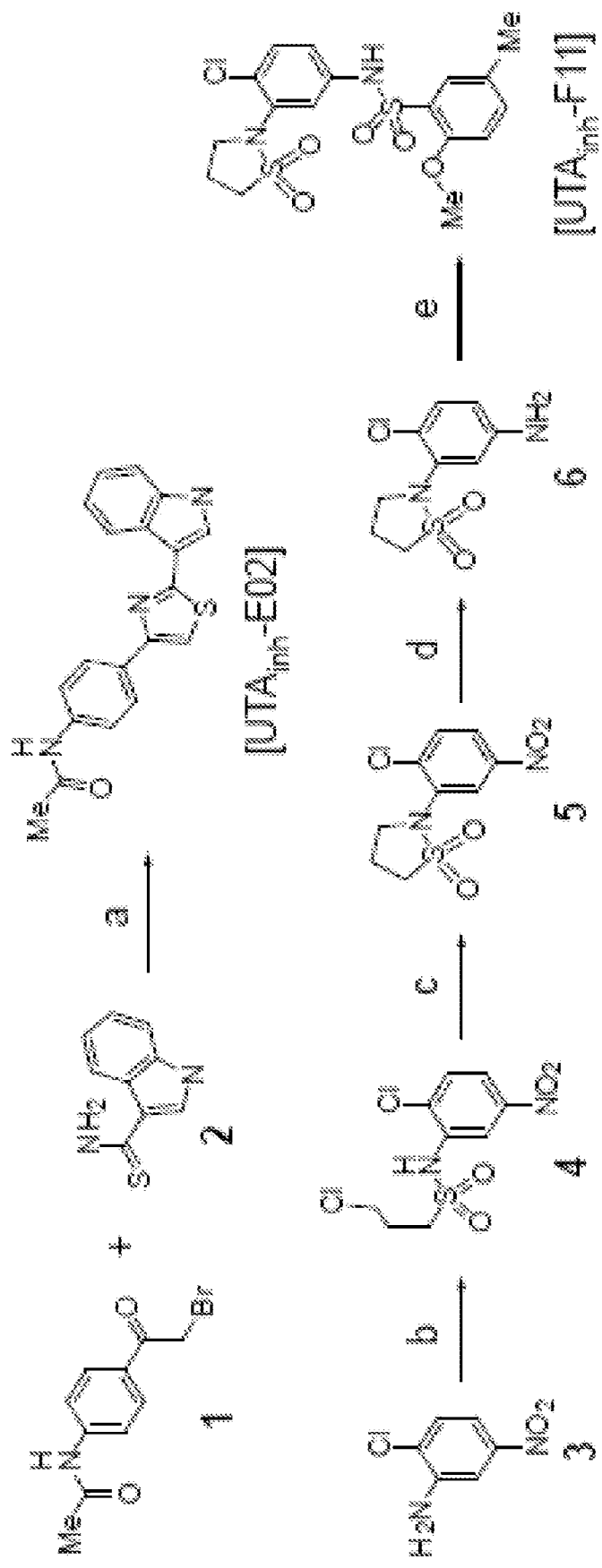

For further analysis, $UTA_{inh}$-E02 and $UTA_{inh}$-F11 were re-synthesized, purified to >99%, and characterized. Condensation of commercially available N-4-(bromoacetylphenyl)acetamide 1 and indolylthiocar-boxamide 2 gave $UTA_{inh}$-E02 in moderate yield (FIG. 2D, top). Synthesis of 3-γ-sultam-1-benzosulfonamidebenzene $UTA_{inh}$-F11 was achieved in four steps (FIG. 2D, bottom). Commercial 2-chloro-5-nitroaniline 3 was sulfonated with 3-chloropropylsulfonyl chloride to give sultam precursor 4, which was cyclized under basic condition using $K_2CO_3$ to yield nitro-γ-sultam 5. Palladium-catalyzed reduction under atmospheric hydrogen efficiently converted nitro-γ-sultam 5 to amino-γ-sultam 6. Finally, condensation of 6 with 2-methoxy-5-methylbenzosulfonyl chloride under basic conditions gave $UTA_{inh}$-F11 in good yield.

No biological activities of a γ-sultam and benzosulfonamide with 1,3-diaminobenzene linkage, as required for UT-A1 inhibition, have been reported. SAR analysis of the γ-sultambenzosulfonamide analogs showed that both the geometry and polarity of substituents are important for inhibition. The 1,4-diaminobenzene linkage resulted in loss of activity, and the activity of 1,3-diaminobenzene analogs depended on the phenylsulfonamide substituents, with greater activity of ortho-methoxy and methyl substituents and reduced activity with para-methoxy, halide and methyl substituents. For class E inhibitors, $UTA_{inh}$-E02 has been reported as a PIM-1 kinase inhibitor with micromolar potency (see, e.g., Ren et al. (2011) *J Chem Inf Model.* 51, 1364-1375), and the more general arylthiazole scaffold is reported to have anti-microbial (see, e.g., Bondock et al. (2013) *Eur J Med Chem.* 62, 270-279) and anti-tumor activities (see, e.g., Diana et al. (2011) *Chem Med Chem.* 6, 1300-1309).

TABLE 1

Structure-activity analysis of class E and F inhibitors.

| Class | Inhibitor | $R^1$ | $R^2$ | $R^3$ | $R^4$ | $IC_{50}$ (µM) UT-A1 | UT-B |
|---|---|---|---|---|---|---|---|
| E  | $UTA1_{inh}$-E01 | phenyl | — | — | — | 3 | 50 |
| | $UTA1_{inh}$-E02 | 2-indole | — | — | — | 1 | 50 |
| | $UTA1_{inh}$-E03 | Me | — | — | — | >50 | >50 |

TABLE 1-continued

Structure-activity analysis of class E and F inhibitors.

| Class | Inhibitor | $R^1$ | $R^2$ | $R^3$ | $R^4$ | IC$_{50}$ (μM) UT-A1 | UT-B |
|---|---|---|---|---|---|---|---|
| F | UTA1$_{inh}$-F01 | H | H | 2-MeO, 5-Me | — | 1 | 6 |
|   | UTA1$_{inh}$-F02 | H | H | 2,5-Me | — | 15 | >75 |
|   | UTA1$_{inh}$-F03 | H | H | 2,4,5-Me | — | 3 | 15 |
|   | UTA1$_{inh}$-F04 | H | H | 2-MeO, 5-F | — | 5 | >75 |
|   | UTA1$_{inh}$-F05 | H | H | 2-MeO, 4-Me, 5-Me | — | 3 | 20 |
|   | UTA1$_{inh}$-F06 | H | Me | 2,5-Me | — | 10 | >75 |
|   | UTA1$_{inh}$-F07 | H | Me | 2-MeO, 5-F | — | 15 | >75 |
|   | UTA1$_{inh}$-F08 | H | Me | 2-MeO, 4-Me, 5-Me | — | 30 | 20 |
|   | UTA1$_{inh}$-F09 | H | OMe | 2-MeO, 5-Me | — | 1 | 8 |
|   | UTA1$_{inh}$-F10 | H | OMe | 2,5-Me | — | 5 | >75 |
|   | UTA1$_{inh}$-F11 | Cl | H | 2-MeO, 5-Me | — | 1 | 10 |
|   | UTA1$_{inh}$-F12 | Cl | H | 2,5-MeO | — | 5 | 50 |
|   | UTA1$_{inh}$-F13 | Cl | H | 2-MeO, 4-Me, 5-Me | — | 8 | 50 |
| F | UTA1$_{inh}$-F14 | — | — | 2-MeO, 5-Me | Me | 20 | 50 |
|   | UTA1$_{inh}$-F15 | — | — | 2-MeO, 5-Me | Me | 3 | 12 |
|   | UTA1$_{inh}$-F16 | — | — | 2-MeO, 4-Me, 5-Me | n-Pr | 10 | 12 |
|   | UTA1$_{inh}$-F17 | — | — | 2-MeO, 5-Cl | n-Pr | 2.5 | 6 |
|   | UTA1$_{inh}$-F18 | — | — | 2-MeO, 5-Me | Et | 20 | 5 |
|   | UTA1$_{inh}$-F19 | — | — | 2-MeO, 4-Me, 5-Me | Et | 6 | 12 |
|   | UTA1$_{inh}$-F20 | — | — | 2-MeO, 5-Et | Et | 6 | 10 |

Example 7

In Vitro Characterization of UT-A1 Inhibition

Figure 3A:
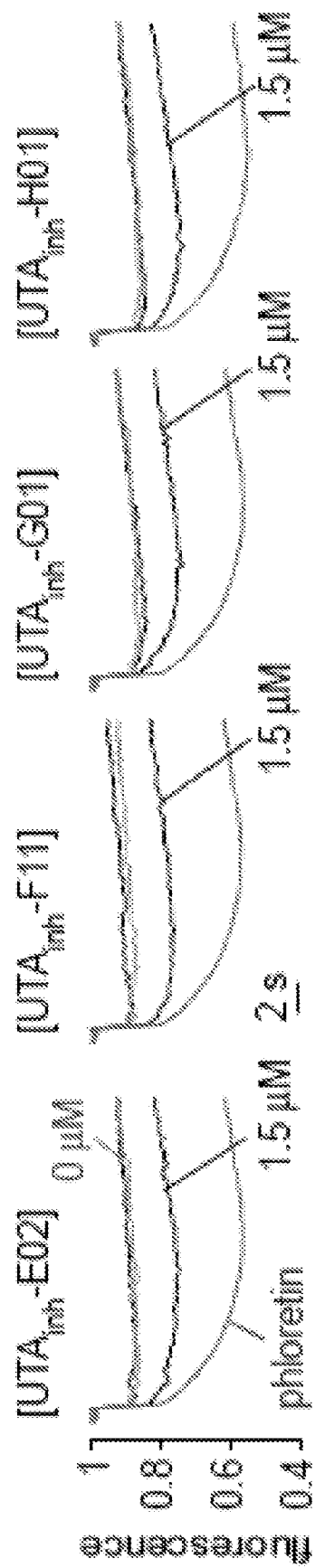
FIGS. 3A-3E show in vitro characterization of UT-A inhibitors.
Figure 3B:
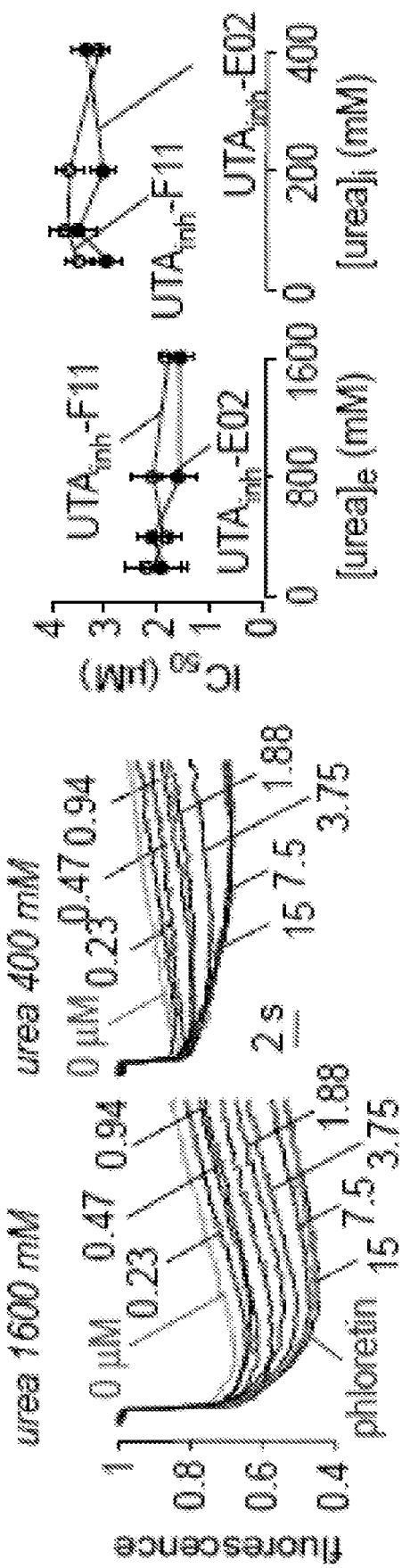

Inhibitor reversibility was studied by incubation of the UT-A1-expressing cells with compounds for 15 min and washing, followed by assay of UT-A1 inhibition. UT-A1 urea transport after inhibitor washout was the same as before inhibitor addition for all compounds (FIG. 3A), indicating full reversibility. Inhibitor competition with urea, as might occur by steric hindrance if the inhibitor and urea occupied physically overlapping sites on the UT-A1 protein, was studied from the urea concentration-dependence of apparent inhibitor IC$_{50}$. Studies were done with zero urea inside cells initially and different urea concentrations outside, and with different urea concentrations inside cells initially and the same inward urea gradient. FIG. 3B shows similar IC$_{50}$ values with different urea concentrations under each set of conditions, providing evidence for a non-competitive inhibition mechanism, which is desirable, as urea concentration is very high in renal inner medulla.

Figure 3C:
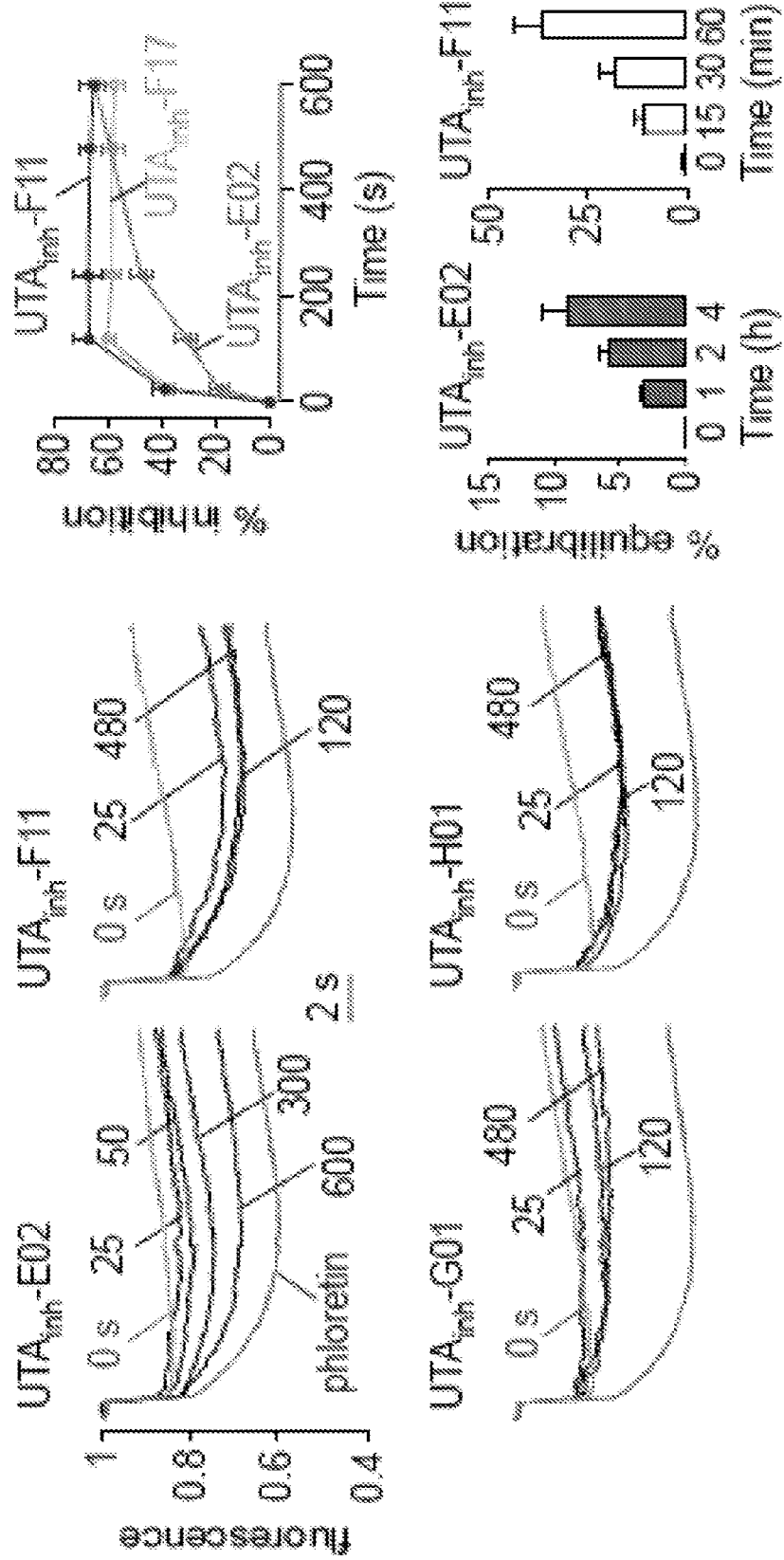

To further evaluate the potential site of inhibitor action, the kinetics of UT-A1 inhibition was measured by assay of UT-A1 inhibition at different times after compound addition. UTA$_{inh}$-E02 inhibition occurred over minutes, suggesting an intracellular site of action, whereas inhibition by F-class compounds was more rapid and would be consistent with an extracellular site of action if their transport into cells is slow compared with their inhibition kinetics (FIG. 3C, left and right, top). To assess inhibitor membrane permeability transport of UTA$_{inh}$-E02 and UTA$_{inh}$-F11 across MDCK monolayers grown on porous filters by LC/MS was measured. Transport of UTA$_{inh}$-F11 was much faster than that of UTA$_{inh}$-E02 (FIG. 3C, right lower panel), with computed transepithelial permeability coefficients of $7 \times 10^{0.7}$ and $1.1 \times 10^{-5}$ cm/s, respectively. From surface-to-volume considerations, the equilibration times were computed of UTA$_{inh}$-E02 and UTA$_{inh}$-F11 to be 250 and 14 s, respectively, in MDCK cells, which are consistent with intracellular sites of action of both inhibitors.

Figure 3D:
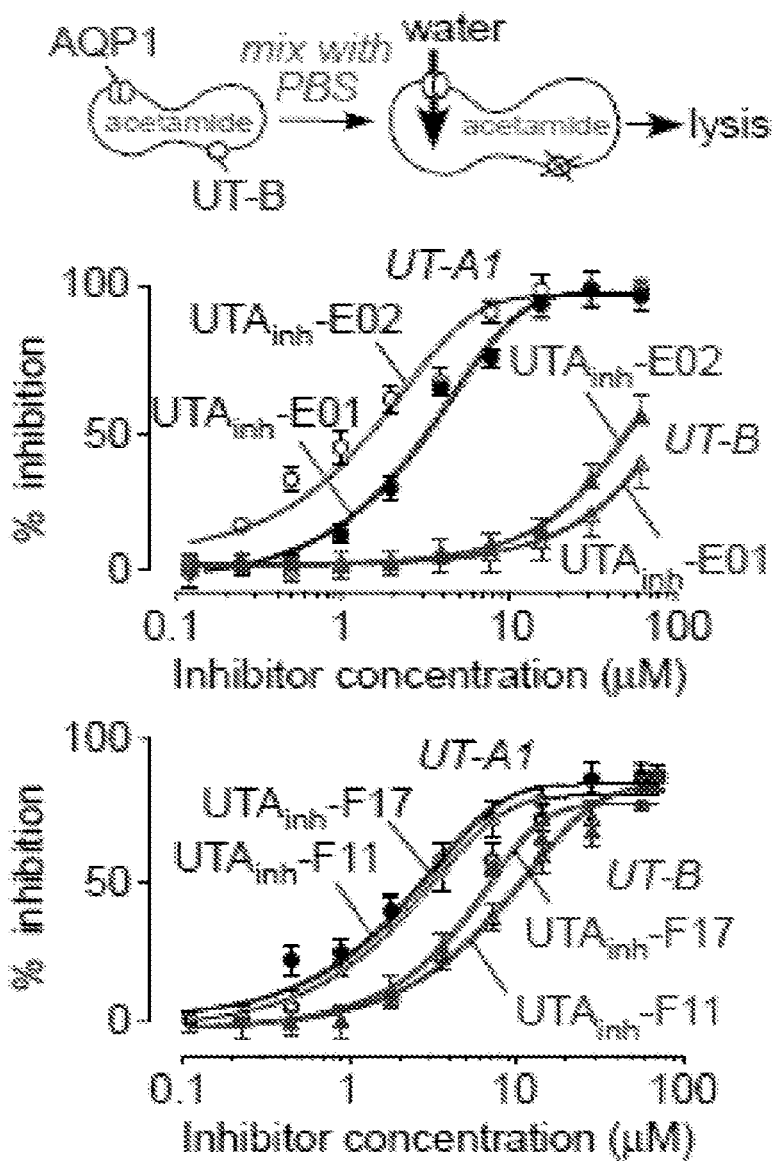

Inhibitor selectivity for rat UT-A1 versus UT-B was investigated using an erythrocyte lysis assay of rat UT-B urea transport, which involved measurement of hypotonic lysis (by near-infrared absorbance) of acetamide-loaded erythrocytes following rapid dilution into acetamide-free buffer. Concentration-inhibition curves in FIG. 3D (top) show high selectivity of UTA$_{inh}$-E01 and UTA$_{inh}$-E02 for UT-A1 inhibition; data in FIG. 3D (bottom) shows moderate UT-A1 versus UT-B selectivity for class F compounds.

Figure 3E:
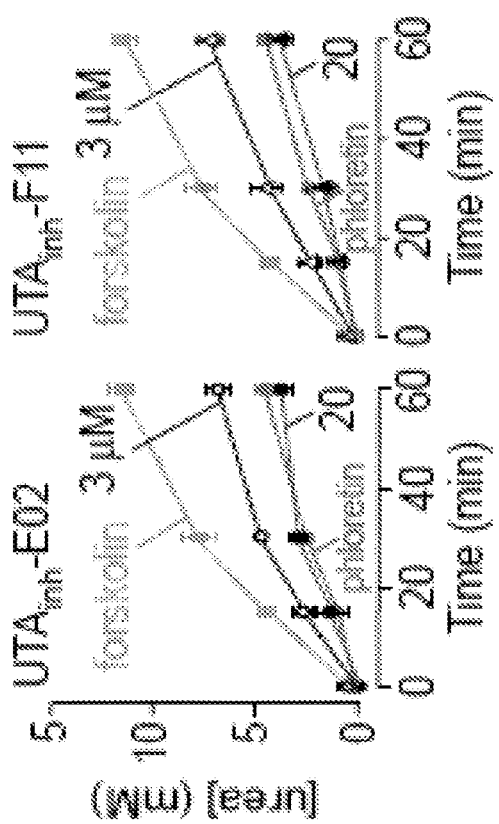

Last, to verify UT-A1 inhibition using an independent cell-based assay that does not rely on water transport or fluorescent dyes, urea transport was measured in UT-A1-transfected MDCK cells cultured on porous filters. Transepithelial urea transport from the basolateral to the apical solution was measured by enzymatic assay of urea in the apical solution following urea addition to the basal-facing solution. Urea permeability in this cell model was increased by forskolin, and reduced by high-concentrations (20 μM) of UTA$_{inh}$-E02 or UTA$_{inh}$-F11 to that of phloretin-treated cells (FIG. 3E); inhibitor concentrations of 3 μM, near their IC$_{50s}$ found in plate reader assays, produced ~50% inhibition.

Computational modeling was done to identify putative binding sites and bound conformations of $UTA_{inh}$-E02 and $UTA_{in}$-F11. Structures for rat UT-A1 and UT-B were generated by homology modeling based on the high-resolution X-ray crystal structure of bovine UT-B solved at 2.5 Å (PDB=4EZD) (see, e.g., Levin et al. (2012) *Proc Natl Acad Sci USA*. 109, 11194-199). There is at present no structural information on UT-A proteins, nor is there a high-resolution structure data for rat UT-B. Several structural features were observed in the bovine UT-B X-ray crystal structure, including low energy binding sites for urea, identified as $S_o$ and $S_i$, adjacent to hydrogen bond acceptors, $Gln^{227}$ and $Gln^{63}$, respectively, as well as a narrow constriction region identified as $S_m$, consisting of $Thr^{334}$ and $Thr^{172}$ (see, e.g., Halgren, T. A. (1996) *J Comp Chem.* 17, 490-519). Notably, our homology models of rat UT-A and UT-B contained homologous residues corresponding to these sites, and were positioned similarly in the central pore region. In the model of rat UT-A, the $S_o$ and $S_i$ sites were adjacent to $Gln^{763}$ and $Gln^{599}$, respectively, while the $S_m$ constriction site consists of $Thr^{870}$ and $Thr^{708}$.

Ligand and receptor preparation, as well as docking simulations, were performed with the OpenEye Scientific suite of utilities, including the software OMEGA (see, e.g., Hawkins et al. (2010) *J Chem Inf Model.* 50, 572-584) and FRED (v2.2.5; McGann, M. (2012) FRED and HYBRID docking performance on standardized datasets. *J. Comput Aided Mol.* 26, 897-906). $UTA_{inh}$-E02 and $UTA_{inh}$-F11 were docked into the extracellular and cytoplasmic domains of rat UT-A1 and UT-B homology models. Active inhibitors docked into the extracellular domain, as well as a selection of inactive inhibitor analogs docked into either domain, showed low-energy binding poses, and appeared to bind non-specifically. Docked conformations of $UTA_{inh}$-E02 and $UTA_{inh}$-F11 are presented in FIG. 4. The lowest energy docked pose of arylthiazole $UTA_{inh}$-E02 into rat UT-A1 orients the indole ring into the pore in the vicinity of $Gln^{599}$ at position $S_i$, with the central thiazole and attached aromatic ring surrounded by several hydrophobic residues lining the outer region of the pore, including $Leu^{652}$, $Leu^{895}$, $Glu^{572}$, $Phe^{832}$, as well as $Ser^{700}$ (FIG. 4A). The less selective γ-sultambenzosulfonamide $UTA_{inh}$-F11 is shown in its lowest energy docked pose into rat UT-A1 (FIG. 4B) and rat UT-B (FIG. 4C). This class of inhibitors docked best with the substituted aryl sulfonamide motif orienting into the pore, with the 5-atom cyclic sultam motif interacting with the pocket of hydrophobic residues (listed above) that line the outer pore. $UTA_{inh}$-F11 docked in a similar manner into UT-B, with the substituted aryl sulfonamide oriented into the pore, and the cyclic sultam group positioned in the outer hydrophobic pocket.

Example 8

Pharmacological Properties of UT-A Inhibitors in Rats

Figure 5A:
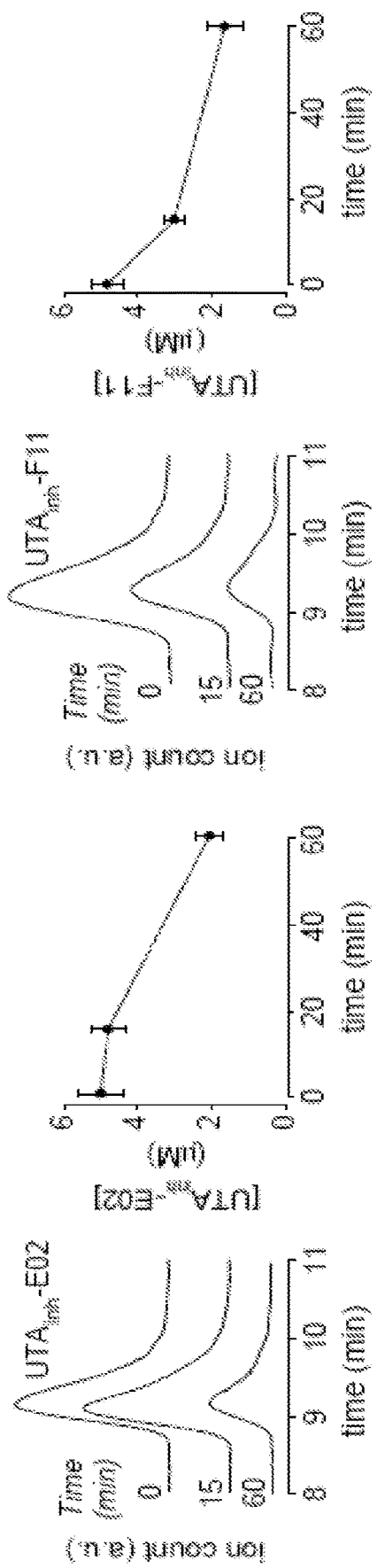
FIGS. 5A-5C describe UT-A inhibitor pharmacology.

In vitro metabolic stability was measured by LC/MS after incubation with rat hepatic microsomes and NADPH. FIG. 5A shows the kinetics of disappearance of the original (non-metabolized) inhibitors $UTA_{inh}$-E02 and $UTA_{inh}$-F11. At 60 min ~50% metabolism was found, which represents reasonable in vitro metabolic stability, much better than that for several other inhibitor classes where the $t_{1/2}$ for compound disappearance was 15 min or less (data not shown).

Figure 5B:
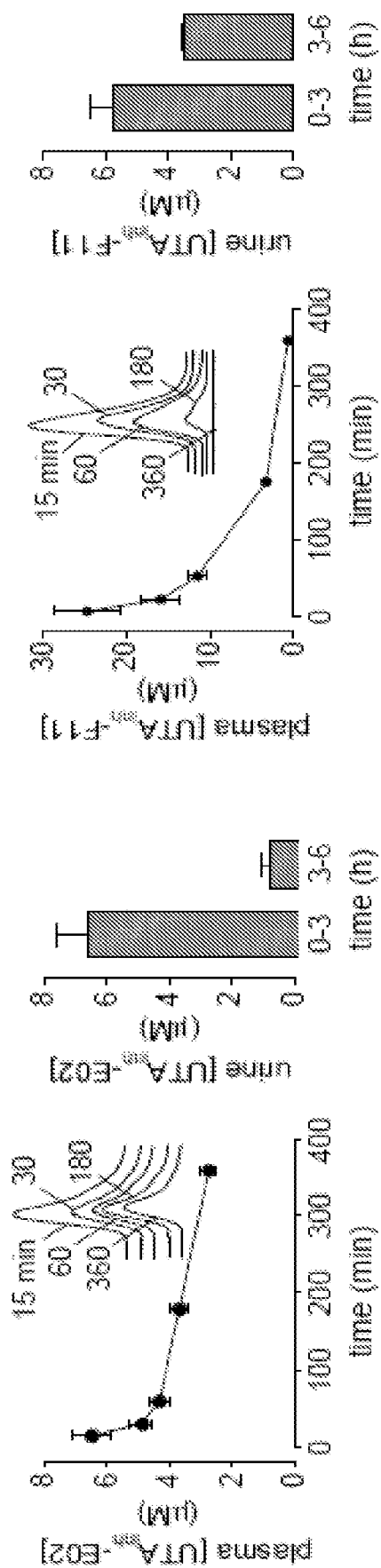

Several vehicles and administration routes were tested in order to give predicted therapeutic inhibitor concentrations in blood and urine. Selection of vehicle for administration of $UTA_{inh}$-E02 was challenging because of its limited solubility, as various combinations of vehicles gave low (<<1 µM) plasma and urine concentrations after intraperitoneal, subcutaneous or oral administration of up to 100 mg/kg. Intravenous administration of 20 mg/kg of $UTA_{inh}$-E02 (5 mg/mL in saline, 20% dimethylacetamide, 40% 2-hydroxypropyl γ-cyclodextrin) to rats yielded ~6 µM plasma and ~3 µM urine levels initially (FIG. 5B, left), with plasma elimination $t_{1/2}$~4.5 h. $UTA_{inh}$-F11 dissolved well in 20% dimethylacetamide, 0.6 mg/mL NaOH in saline. Because of the alkaline pH of the administered compounds the vehicle control for $UTA_{inh}$-F11 was 20% dimethylacetamide and 1.2 mg/mL $NaHCO_3$ in saline to give identical pH. Intravenous administration of 20 mg/kg $UTA_{inh}$-F11 to rats yielded to higher initial plasma levels than $UTA_{inh}$-E02, but lower $t_{1/2}$-1 h (FIG. 5B, right). Urine levels of $UTA_{inh}$-F11 were >3 µM over 6 h.

Figure 5C:
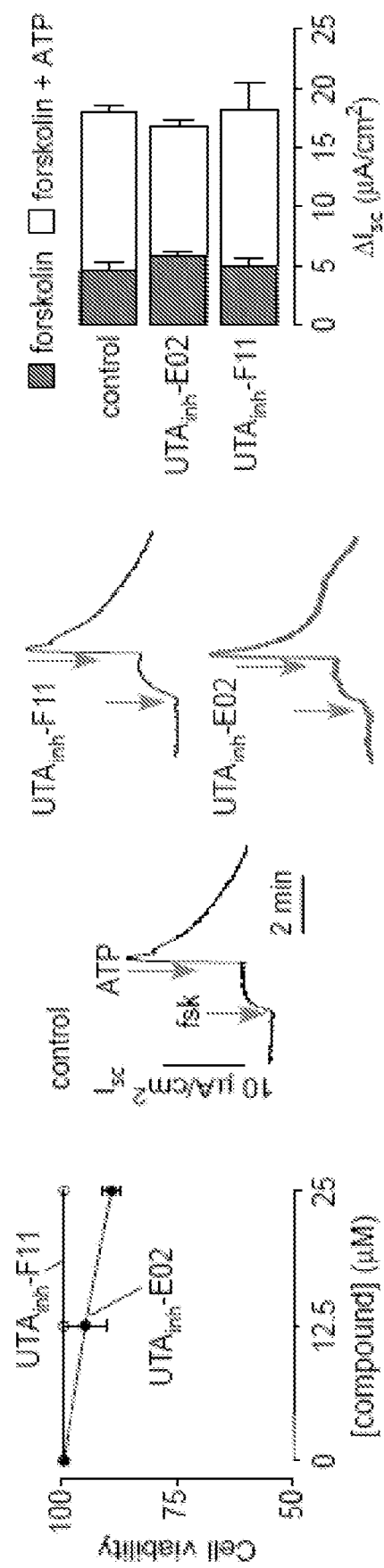

Compound toxicity was evaluated by compound incubation for 24 h with MDCK cell cultures followed by Alamar blue assay. FIG. 5C (left) shows little toxicity of $UTA_{inh}$-E02 and $UTA_{inh}$-F11 at up to 25 µM, near their solubility limits. To assess potential ion channel off-target effects, short-circuit current was measured in MDCK cells in response to cAMP (forskolin) and calcium (ATP) agonists (FIG. 5C, right), which depends on the actions of multiple anion (CFTR, calcium-activated chloride channels) and cation ($K^+$, $Na^+$) channels. Neither inhibitor at 20 µM altered short-circuit current.

Example 9

Diuretic Action of UT-A Inhibitors in Rats

Figure 6A:
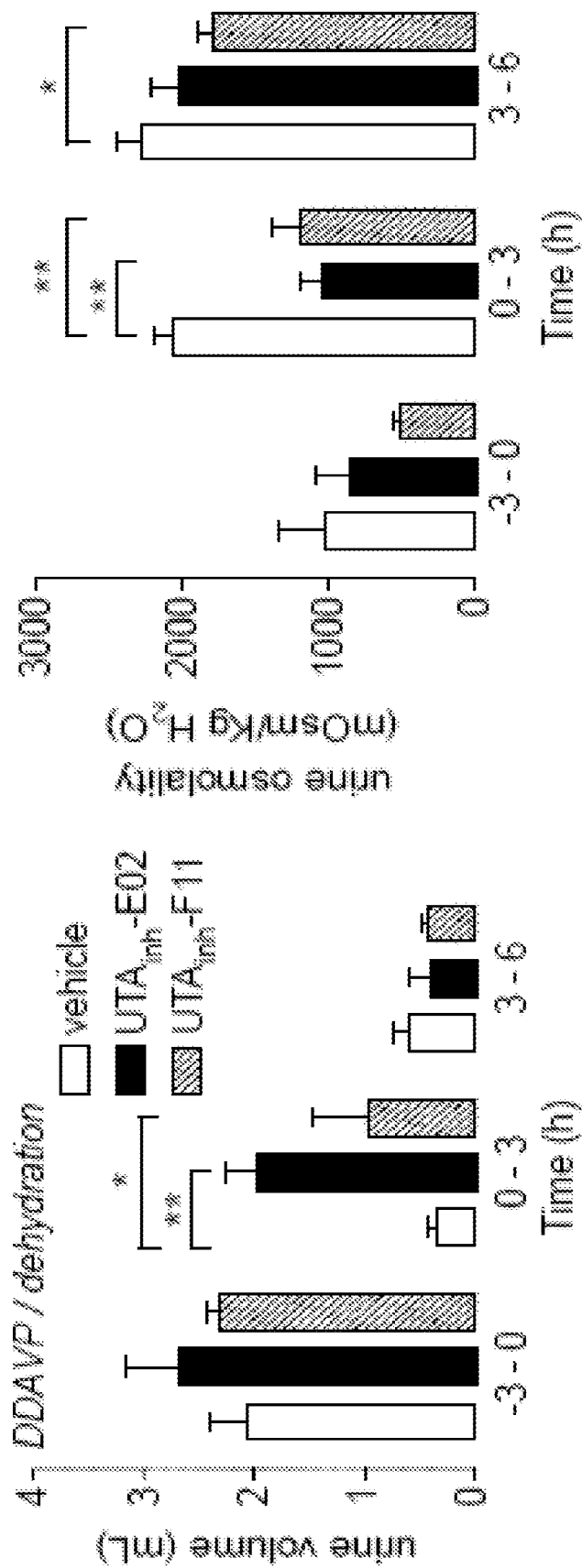
FIGS. 6A-6C illustrate diuretic action of UT-A inhibitors in rats.
Figure 6B:
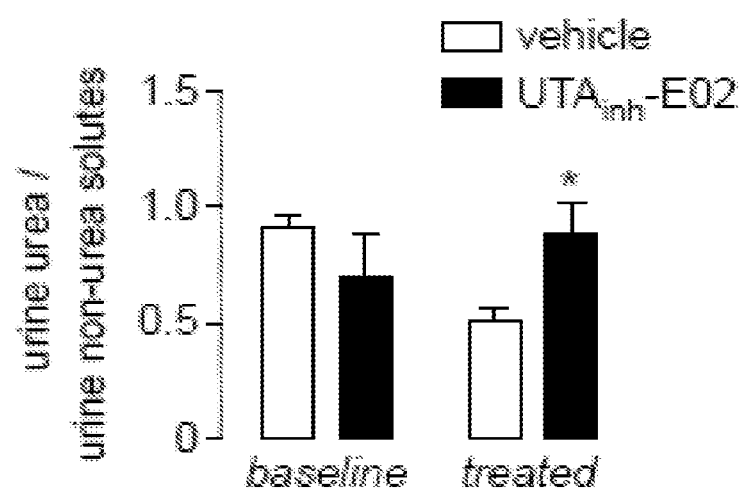

Diuretic efficacy was tested in rats under two different conditions. Inhibitor effects on maximum urinary concentrating ability was studied in rats administered the V2-selective agonist dDAVP at 4 µg/kg every 3 hours. Inhibitors were administered intravenously at 20 mg/kg as done in the pharmacokinetics experiments above. FIG. 6A shows similar urine volume and osmolality of vehicle and treated groups prior to inhibitor administration (-3 to 0 h). Each inhibitor produced a marked increase in volume and reduction in osmolality in urine collected over 0-3 h. Little difference was seen at 3-6 h, which is consistent with pharmacokinetics data, showing reversible inhibitor action. FIG. 6B shows that the diuresis produced by $UTA_{inh}$-E02 was relatively urea-selective, as shown by the increased ratio of urea vs. non-urea solutes in urine after inhibitor treatment.

Figure 6C:
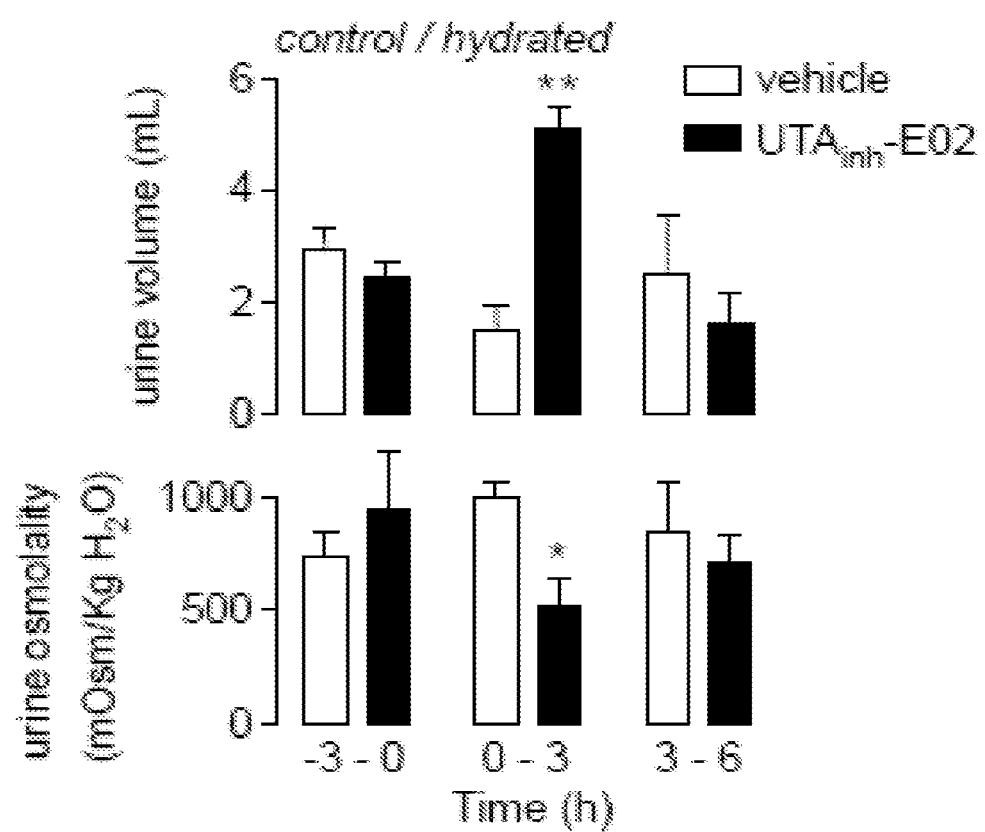

In a separate set of studies $UTA_{inh}$-E02 was tested in control, hydrated rats. FIG. 6C shows significantly increased urine volume and reduced urine osmolality at 0-3 h after $UTA_{inh}$-E02 administration. Urine volume and osmolality returned to near baseline in the 3-6 h collection.

REFERENCES

1. Bankir, L., and Yang, B. (2012) New insights into urea and glucose handling by the kidney, and the urine concentrating mechanism. *Kidney Internat.* 81, 1179-1198
2. Sands, J M., and Layton, H E. (2009) The physiology of urinary concentration: an update. *Semin Nephrol.* 29, 178-195
3. Sands, J M. (2007) Critical role of urea in the urine-concentrating mechanism. *J Am Soc Nephrol.* 18, 670-671
4. Lei, T., Zhou, L., Layton, A T., Zhou, H., Zhao, X., Bankir, L., and Yang, B. (2011) Role of thin descending limb urea transport in renal urea handling and the urine concentrating mechanism. *Am J Physiol Renal Physiol.* 301, F1251-F1259
5. Pannabecker, T L. (2013) Comparative physiology and architecture associated with the mammalian urine concentrating mechanism: role of inner medullary water and urea transport pathways in the rodent medulla. *Am J Physiol Regul Integr Comp Physiol.* 304, R488-R503
6. Bagnasco, S M. (2003) Gene structure of urea transporters. *Am J Physiol Renal Physiol.* 284, F3-F10
7. Doran, J J., Klein, J D., Kim, Y H., Smith, T D., Kozlowski, S D., Gunn, R B., and Sands, J M. (2006) Tissue distribution of UT-A and UT-B mRNA and protein in rat. *Am J Physiol Regul Integr Comp Physiol.* 290, R1446-R1459
8. Klein, J D., Blount, M A., and Sands, J M. (2012) Molecular mechanisms of urea transport in health and disease. *Pflugers Arch.* 464, 561-572
9. Smith, C P. (2009) Mammalian urea transporters. *Exper Physiol.* 94, 180-185
10. Stewart, G. (2011) The emerging physiological roles of the SLC14A family of urea transporters. *Br J Pharmacol.* 164, 1780-1792
11. Fenton, R A., Stewart, G S., Carpenter, B., Howorth, A., Potter, E A., Cooper, G J., and Smith, C P. (2002) Characterization of mouse urea transporters UT-A1 and UT-A2. *Am J Physiol Renal Physiol.* 283, F817-F825
12. Fenton, R A. (2009) Essential role of vasopressin-regulated urea transport processes in the mammalian kidney. *Pflugers Arch.* 458, 169-177
13. Shayakul, C., Clémençon, B., and Hediger, M A. (2013) The urea transporter family (SLC14): physiological, pathological and structural aspects. *Mol Aspects Med.* 34, 313-322
14. Shayakul, C., and Hediger, M A. (2004) The SLC14 gene family of urea transporters. *Pflugers Arch.* 447, 603-609
15. Sands, J. M. (2004) Renal urea transporters. *Curr Opin Nephrol Hypertens.* 13, 525-532
16. Fenton, R A., Chou, C L., Stewart, G S., Smith, C P., and Knepper, M A. (2004) Urinary concentrating defect in mice with selective deletion of phloretin-sensitive urea transporters in the renal collecting duct. *Proc Natl Acad Sci USA.* 101, 7469-7474
17. Fenton, R A., Flynn, A., Shodeinde, A., Smith, C P., Schnermann, J., and Knepper, M A. (2005) Renal phenotype of UT-A urea transporter knockout mice. *J Am Soc Nephrol.* 16, 1583-1592
18. Fenton, R A. (2008) Urea transporters and renal function: lessons from knockout mice. *Curr Opin Nephrol Hypertens.* 17, 513-518
19. Uchida, S., Sohara, E., Rai, T., Ikawa, M., Okabe, M., and Sasaki, S. (2005) Impaired urea accumulation in the inner medulla of mice lacking the urea transporter UT-A2. *Mol Cell Biol.* 25, 7357-7363
20. Klein, J D., Frohlich, O., Mistry, A C., Kent, K J., Martin, C F., and Sands, J M. (2013). Transgenic mice expressing UT-A1, but lacking UT-A3, have intact urine concentration ability. *FASEB J* 27, 1111.17 (EB abstract).
21. Yang, B., Bankir, L., Gillespie, A., Epstein, C J., and Verkman, A S. (2002) Urea-selective concentrating defect in transgenic mice lacking urea transporter UT-B. *J Biol Chem.* 277, 10633-10637
22. Liu, Y., Esteva-Font, C., Yao, C., Phuan, P. W., Verkman, A. S., and Anderson, M. O. (2013) 1,1-Difluoroethyl-substituted triazolothienopyrimidines as inhibitors of a human urea transport protein (UT-B): new analogs and binding model. *Bioorgan Med Chem Lett.* 23, 3338-3341
23. Knepper, M. A., and Miranda, C. A. (2013) Urea channel inhibitors: a new functional class of aquaretics. *Kidney Intern.* 83, 991-993.
24. Sands, J. M. (2013) Urea transporter inhibitors: en route to new diuretics. *Chem Biol.* 24, 1201-1202.
25. Sands, J. M., and Layton, H. E. (2014) Advances in understanding the urine-concentrating mechanism. *Annu Rev Physiol.* 10, 387-409
26. Denton, J. S., Pao, A. C., and Maduke, M. (2013) Novel diuretic targets. *Am J Physiol Renal Physiol.* 305, F931-F942
27. Mayrand, R. R., and Levitt, D. G. (1983) Urea and ethylene glycol-facilitated transport systems in the human red cell membrane. Saturation, competition, and asymmetry. *J Gen Physiol.* 81, 221-237
28. Levin, M. H., de la Fuente, R., and Verkman, A. S. (2007) Urearetics: a small molecule screen yields nanomolar potency inhibitors of urea transporter UT-B. *FASEB J.* 21, 551-563
29. Yao, C., Anderson, M. O., Zhang, J., Yang, B., Phuan, P. W., and Verkman, A. S. (2012) Triazolothienopyrimidine inhibitors of urea transporter UT-B reduce urine concentration. *J Am Soc Nephrol.* 23, 1210-1220
30. Anderson, M. O., Zhang, J, Liu, Y., Yao, C., Phuan, P. W., and Verkman, A. S. (2012) Nanomolar potency and metabolically stable inhibitors of kidney urea transporter UT-B. *J Med Chem.* 55, 5942-5950
31. Li, F., Lei, T., Zhu, J., Wang, W., Sun, Y., Chen, J., Dong, Z., Zhou, H., and Yang, B. (2013) A novel small-molecule thienoquinolin urea transporter inhibitor acts as a potential diuretic. *Kidney Internat.* 83, 1076-1086
32. Cil, O., Ertunk, N., and Onur, R. (2012) The diuretic effect of urea analog dimethylthiourea in female Wistar rats. *Hum Exp Toxicol.* 31, 1050-1055
33. Esteva-Font, C., Phuan, P. W., Anderson, M. O., and Verkman, A. S. (2013) A small molecule screen identifies selective inhibitors of urea transporter UT-A. *Chem Biol.* 20, 1235-1244
34. Frohlich, O., Klein, J. D., Smith, P. M., Sands, J. M., and Gunn, R. B. (2006) Regulation of UT-A1-mediated transepithelial urea flux in MDCK cells. *Am J Physiol Cell Physiol.* 291, C600-D606.
35. Galietta, L. J., Haggie, P. M., and Verkman, A. S. (2001) Green fluorescent protein-based halide indicators with improved chloride and iodide affinities. *FEBS Lett.* 499, 220-224
36. Arnold, K., Bordoli, L., Kopp, J., and Schwede, T. (2006) The SWISS-MODEL Workspace: A web based environment for protein structure homology modeling. *Bioinformatics* 22, 195-201
37. Bordoli, L., Kiefer, F., Arnold, K., Benkert, P., Battey, J. and Schwede, T. (2009) Protein structure homology modelling using SWISS-MODEL Workspace. *Nat Prot.* 4, 1-13
38. Levin, E. J., Cao, Y., Enkavi, G., Quick, M., Pan, Y., Tajkhorshid, E., and Zhou, M. (2012) Structure and permeation mechanism of a mammalian urea transporter. *Proc NatlAcad Sci USA.* 109, 11194-11199
39. Halgren, T. A. (1996) Merck molecular force field. I. Basis, form, scope, parameterization, and performance of MMFF94. *J Comp Chem.* 17, 490-519
40. Hawkins, P. C. D., and Nicholls, A. J. (2012) Conformer generation with OMEGA: Learning from the data set and the analysis of failures. *J Chem Inf Model* 52, 2919-2936
41. McGann, M. (2012) FRED and HYBRID docking performance on standardized datasets. *J. Comput Aided Mol.* 26, 897-906

42. Snyder, D. S., Tradtrantip, L., Yao, C., Kurth, M. J., and Verkman, A. S. (2011) Potent, metabolically stable benzopyrimido-pyrrolo-oxazine-dione (BPO) CFTR inhibitors for polycystic kidney disease. *J Med Chem.* 54, 5468-5477

43. Hawkins, P. C. D., Skillman, A. G., Warren, G. L., Ellingson, B. A., Stahl, M. T. (2010). Conformer generation with OMEGA: Algorithm and validation using high quality structures from the protein databank and Cambridge structural database. *J Chem Inf Model.* 50, 572-584

44. Lucien, N., Sidoux-Walter, F., Olives, B., Moulds, J., Le Pennec, P Y., Cartron, J P., and Bailly, P. (1998) Characterization of the gene encoding the human Kidd blood group/urea transporter protein. Evidence for splice site mutations in Jknull individuals. *J Biol Chem.* 273, 12973-12980

45. Sands, J. M., Gargus, J. J., Frohlich, O., Gunn, R. B., and Kokko, J. P. (1992) Urinary concentrating ability in patients with Jk(a-b-) blood type who lack carrier-mediated urea transport. *J Am Soc Nephrol.* 2, 1689-1696

46. Ren, J. X., Li, L. L., Zheng, R. L., Xie, H. Z., Cao, Z. X., Feng, S., Pan, Y. L., Chen, X., Wei, Y. Q., and Yang, S. Y. (2011) Discovery of novel Pim-1 kinase inhibitors by a hierarchical multistage virtual screening approach based on SVM model, pharmacophore, and molecular docking. *J Chem Inf Model.* 51, 1364-1375

47. Bondock, S., Naser, T., and Ammar, Y A. (2013) Synthesis of some new 2-(3-pyridyl)-4,5-disubstituted thiazoles as potent antimicrobial agents. *Eur J Med Chem.* 62, 270-279

48. Diana, P., Carbone, A., Barraja, P., Montalbano, A., Parrino, B., Lopergolo, A., Pennati, M., Zaffaroni, N., and Cirrincione, G. (2011) Synthesis and antitumor activity of 3-(2-phenyl-1,3-thiazol-4-yl)-1H-indoles and 3-(2-phenyl-1,3-thiazol-4-yl)-1H-7-azaindoles. *Chem Med Chem.* 6, 1300-1309

49. Lipinski, C. A., Lombardo, F., Dominy, B. W., Feeney, P. J. (2001) Experimental and computational approaches to estimate solubility and permeability in drug discovery and development settings. *Adv Drug Deliv Rev.* 46, 3-26

50. Veber, D. F., Johnson, S. R., Cheng, H. Y., Smith, B. R., Ward, K. W., and Kopple, K. D. (2002) Molecular properties that influence the oral bioavailability of drug candidates. *J Med Chem.* 45, 2615-2623

The various embodiments described above can be combined to provide further embodiments. All U.S. patents, U.S. patent application publications, U.S. patent applications, foreign patents, foreign patent applications, and non-patent publications referred to in this specification and/or listed in the Application Data Sheet are incorporated herein by reference, in their entirety. This application claims the benefit of U.S. Provisional Application No. 61/991,112 filed May 9, 2014, which U.S. provisional application is incorporated by reference in its entirety. Aspects of the embodiments can be modified, if necessary to employ concepts of the various patents, applications, and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

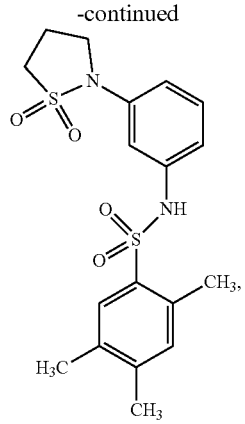

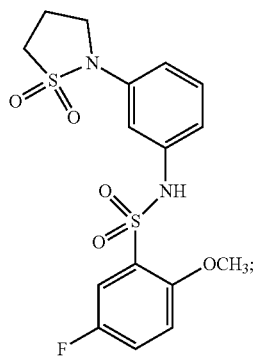

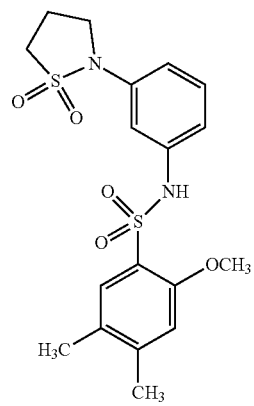

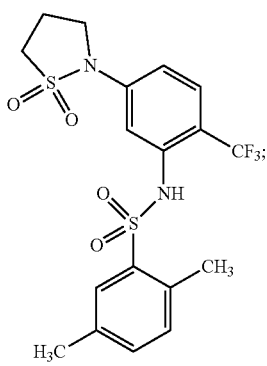

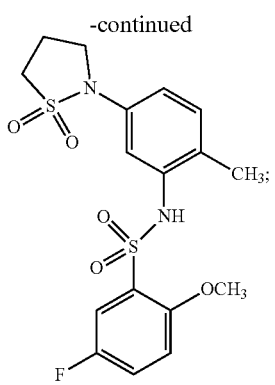
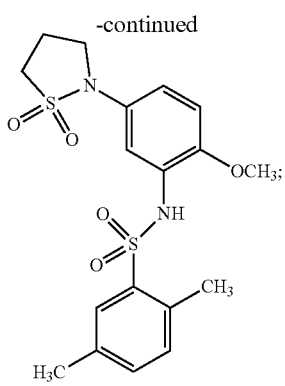

We claim the following:

1. A method for treating a disease or disorder treatable by inhibiting transport of urea in a subject having the disease or disorder, said method comprising administering to the subject pharmaceutical composition comprising a pharmaceutically acceptable excipient and a compound of Formula (II):

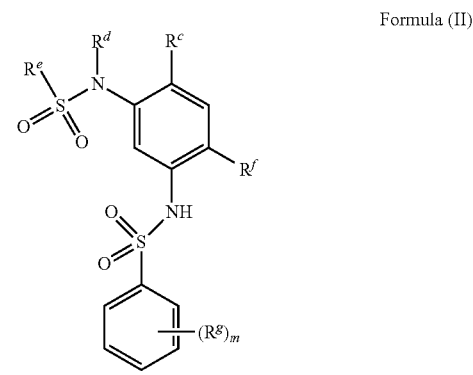

Formula (II)

wherein, m is 0, 1, 2 or 3;

$R^c$ is hydrogen, halo, or $C_{1-3}$alkyl; or $R^c$ and $R^d$, together with the C and N atoms to which they are attached respectively, form a 5-member or 6-member heterocyclyl ring;

$R^e$ is $C_{1-3}$alkyl; or $R^e$ and $R^d$, together with the S and N atoms to which they are attached respectively, form a 5-member or 6-member heterocyclyl ring;

$R^f$ is hydrogen or $C_{1-3}$alkoxy; and $R^g$ is independently, at each occurrence, $C_{1-3}$alkyl, $C_{1-3}$alkoxy, or halo, a stereoisomer, enantiomer or tautomer thereof, a pharmaceutically acceptable salt thereof, or a prodrug thereof.

2. The method of claim 1, wherein the compound has a structure represented by Formula (IIa):

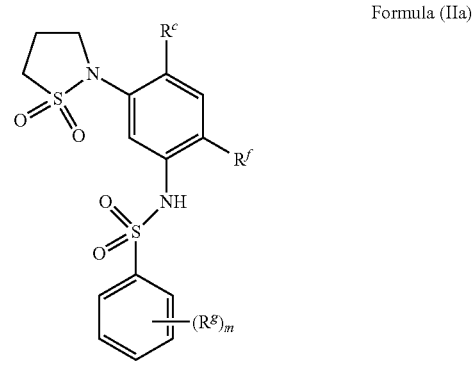

Formula (IIa)

wherein, m is 0, 1, 2 or 3;

$R^c$ is hydrogen, halo or $C_{1-3}$alkyl;

$R^f$ is hydrogen or $C_{1-3}$alkoxy; and $R^g$ is independently, at each occurrence, $C_{1-3}$alkyl, $C_{1-3}$alkoxy, or halo.

3. The method of claim 2, wherein m is 2 or 3; $R^c$ is hydrogen or chloro; $R^f$ is methoxy; and $R^g$ is independently, at each occurrence, methyl, methoxy, fluoro or chloro.

4. The method of claim 1 wherein the compound has a structure represented by Formula (IIb):

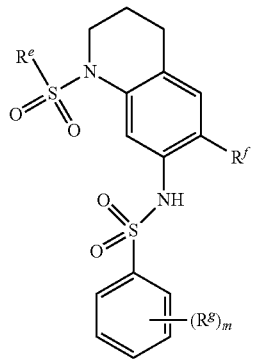

Formula (IIb)

wherein, m is 0, 1, 2 or 3;

$R^e$ is $C_{1-3}$alkyl;

$R^f$ is hydrogen or $C_{1-3}$alkoxy; and $R^g$ is independently, at each occurrence, $C_{1-3}$alkyl, $C_{1-3}$alkoxy, or halo.

5. The method of claim 4, wherein m is 0; $R^e$ is $C_{1-3}$alkyl; and $R^f$ is hydrogen.

6. The method of claim 1 wherein the disease or disorder is (a) refractory edema associated with cirrhosis, nephritic syndrome, acute renal failure, chronic renal insufficiency, or congestive heart failure; (b) syndrome of inappropriate antidiuretic hormone secretion (SIADH); (c) azotemia; (e) fluid retention; (f) hypertension, or (g) abnormal uresis.

7. The method of claim 2 wherein the compound of Formula (IIa) is:

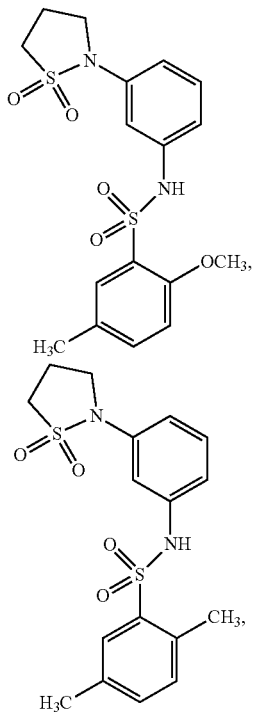

-continued